US012765871B2

(12) United States Patent
Yamada et al.

(10) Patent No.: US 12,765,871 B2
(45) Date of Patent: Oct. 20, 2026

(54) TREATMENT TOOL FOR ENDOSCOPE

(71) Applicant: OLYMPUS MEDICAL SYSTEMS CORP., Tokyo (JP)

(72) Inventors: Kotaro Yamada, Tachikawa (JP); Yusuke Shiota, Machida (JP); Hiromasa Kato, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 937 days.

(21) Appl. No.: 17/975,944

(22) Filed: Oct. 28, 2022

(65) Prior Publication Data

US 2023/0136593 A1 May 4, 2023

Related U.S. Application Data

(60) Provisional application No. 63/273,166, filed on Oct. 29, 2021.

(51) Int. Cl.
*A61B 17/00* (2006.01)
*A61B 17/02* (2006.01)
(Continued)

(52) U.S. Cl.
CPC .... *A61B 17/00234* (2013.01); *A61B 17/0218* (2013.01); *A61B 18/14* (2013.01); *A61M 31/00* (2013.01); *A61B 1/018* (2013.01); *A61B 2017/00269* (2013.01); *A61B 2017/0034* (2013.01); *A61B 17/32037* (2013.01);
(Continued)

(58) Field of Classification Search
CPC ........... A61B 2018/00601; A61B 2018/00982; A61B 18/1492; A61B 2017/00269; A61B 1/018; A61B 2218/002; A61B 17/320016; A61B 2017/0034; A61B 17/3478; A61B 17/00234; A61B 17/0218; A61B 17/32037; A61B 2018/00494; A61B 2217/007; A61B 2018/00029; A61B 2018/1253;
(Continued)

(56) References Cited

U.S. PATENT DOCUMENTS

2008/0161792 A1* 7/2008 Wang ................ A61B 18/1492 606/41
2011/0028887 A1 2/2011 Fischer et al.
(Continued)

FOREIGN PATENT DOCUMENTS

CN 111202485 A 5/2002
CN 111447867 A * 7/2020 .......... A61M 16/201
(Continued)

OTHER PUBLICATIONS

Office Action dated May 26, 2026, issued in corresponding Japanese Patent Application No. 2022-170603.

*Primary Examiner* — Wesley G Harris
(74) *Attorney, Agent, or Firm* — Morgan, Lewis & Bockius LLP

(57) ABSTRACT

A treatment tool includes a sheath, a hollow pipe extending in the sheath and an elastically deformable constricting member. The hollow pipe includes a flow channel formed in a direction of a longitudinal axis of the hollow pipe and extending between a distal end of the hollow pipe and a proximal end of the hollow pipe. The elastically deformable constricting member includes a first end that is reversibly insertable into the flow channel.

19 Claims, 16 Drawing Sheets

(51) Int. Cl.

| | |
|---|---|
| ***A61B 18/14*** | (2006.01) |
| ***A61M 31/00*** | (2006.01) |
| *A61B 1/018* | (2006.01) |
| *A61B 17/3203* | (2006.01) |
| *A61B 17/34* | (2006.01) |
| *A61B 18/00* | (2006.01) |

(52) U.S. Cl.
CPC . *A61B 17/3478* (2013.01); *A61B 2018/00494* (2013.01); *A61B 2018/00601* (2013.01); *A61B 2018/00982* (2013.01); *A61B 18/1492* (2013.01); *A61B 2217/007* (2013.01); *A61B 2218/002* (2013.01)

(58) Field of Classification Search
CPC .................... A61B 18/12; A61B 18/14; A61B 2018/00482; A61B 2018/00589; A61M 31/00
See application file for complete search history.

(56) References Cited

U.S. PATENT DOCUMENTS

| | | | |
|---|---|---|---|
| 2012/0035607 | A1 | 2/2012 | Karwei |
| 2012/0157906 | A1 | 6/2012 | Underwood et al. |

FOREIGN PATENT DOCUMENTS

| | | | | |
|---|---|---|---|---|
| JP | 2011-516131 | A | 5/2011 | |
| JP | 2012-523863 | A | 10/2012 | |
| JP | 2014-509207 | A | 4/2014 | |
| WO | WO-2009121563 | A2 * | 10/2009 | ......... A61B 17/3203 |
| WO | 2015/053365 | A1 | 4/2015 | |
| WO | WO-2017036479 | A1 * | 3/2017 | ............... A61B 1/05 |

* cited by examiner

TREATMENT TOOL FOR ENDOSCOPE

RELATED APPLICATION DATA

The present disclosure relates to a treatment tool for an endoscope. This application claims benefit from U.S. Patent Provisional Application No. 63/273,166, filed Oct. 29, 2021, the contents of which are incorporated herein by reference.

FIELD OF THE DISCLOSURE

The disclosure relates to an endoscope treatment tool.

BACKGROUND

In the related art, in an endoscopic treatment such as endoscopic submucosal dissection (ESD) or the like, a treatment tool for an endoscope used in incision or dissecting such as a high frequency knife, or the like a treatment tool for an endoscope used in local injection, a treatment tool for an endoscope used in hemostasis, or the like, is used.

Chinese Unexamined Patent Application, First Publication No. 111202485A and Japanese Translation of PCT International Application Publication No. 2012-523863 disclose treatment tools for endoscopes capable of performing incision treatment and local injection treatment of a tissue.

In endoscopic treatment such as ESD or the like, additional local injection can be performed after an endoscope treatment tool for local injection (for example, a local injection needle) is pulled out. In such a case, additional local injection is performed on the submucosa using a high frequency knife having a water supply function.

SUMMARY

A treatment tool includes a sheath, a hollow pipe extending in the sheath and an elastically deformable constricting member. The hollow pipe includes a flow channel formed in a direction of a longitudinal axis of the hollow pipe and extending between a distal end of the hollow pipe and a proximal end of the hollow pipe. The elastically deformable constricting member includes a first end that is reversibly insertable into the flow channel.

DETAILED DESCRIPTION OF THE DISCLOSURE

First Embodiment

An endoscope treatment system 300 according to a first embodiment of the present disclosure will be described with reference to FIG. 1 to FIG. 5.

Figure 1:
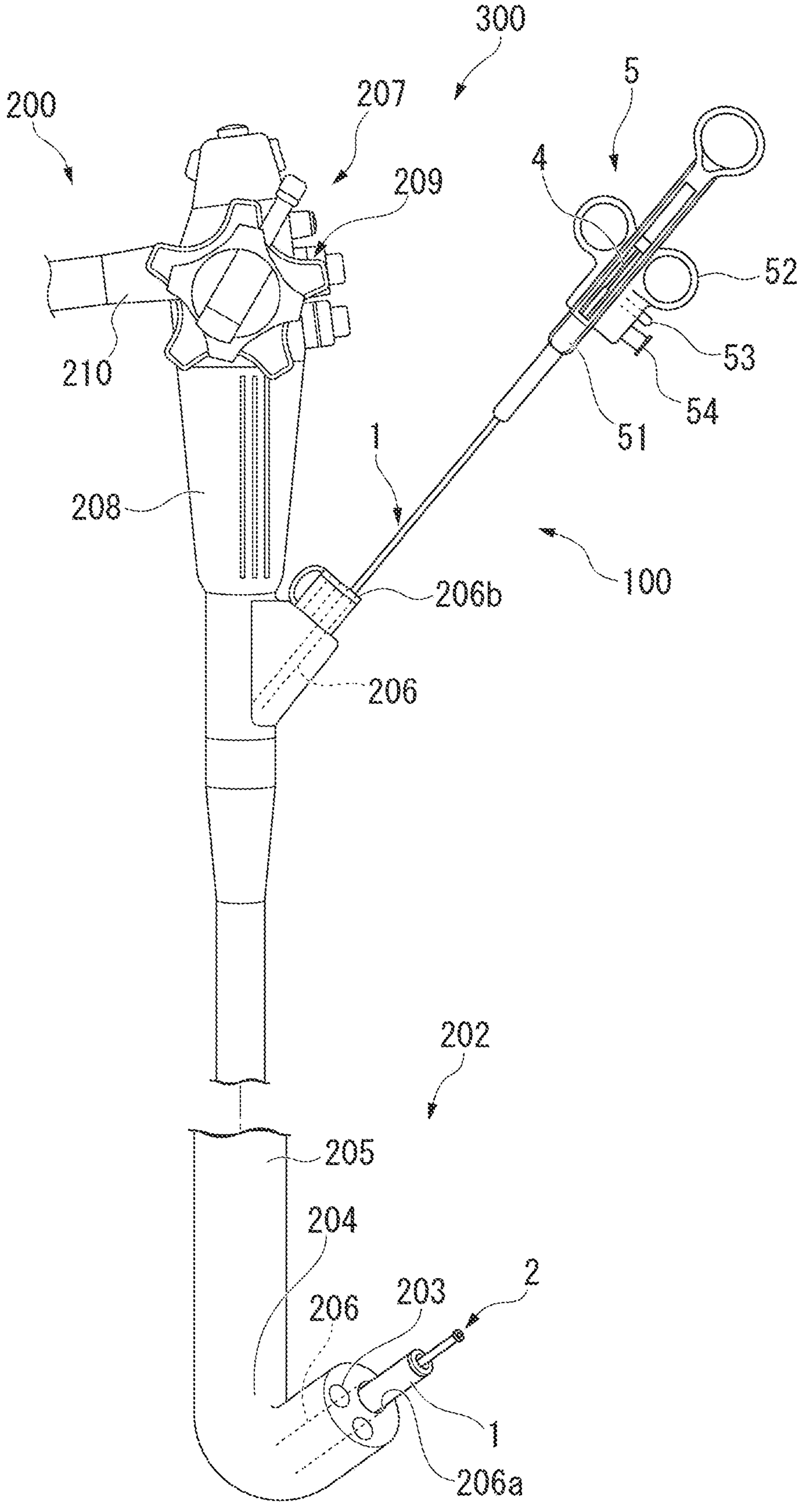
FIG. 1 is an overall view of an endoscope treatment system according to a first embodiment.

FIG. 1 is an overall view of the endoscope treatment system 300 according to the embodiment.

[Endoscope Treatment System 300]

As shown in FIG. 1, the endoscope treatment system 300 includes an endoscope 200 and a treatment tool 100.

The treatment tool 100 is used to be inserted into the endoscope 200 and used.

[Endoscope 200]

The endoscope 200 is a known flexible endoscope. The endoscope 200 includes an insertion part 202 inserted into the body from a distal end thereof, and an operation part 207 attached to a proximal end of the insertion part 202.

The insertion part 202 has an imaging part 203, a bending part 204, and a flexible part 205. The imaging part 203, the bending part 204, and the flexible part 205 are disposed in the insertion part 202 in sequence from the distal end.

A channel 206 into which the treatment tool 100 is inserted is provided in the insertion part 202. A distal opening section 206*a* of the channel 206 is formed in the distal end of the insertion part 202.

The imaging part 203 includes an imaging device such as a CCD, a CMOS, or the like. The imaging part 203 is configured to image an area that is a treatment object. The imaging part 203 can image a hollow pipe 2 of the treatment tool 100 in a state in which the treatment tool 100 protrudes from the distal opening section 206*a* of the channel 206.

The bending part 204 is curved according to an operation of the operation part 207 by an operator. The flexible part 205 is a tubular area having flexibility.

The operation part 207 is connected to the flexible part 205. The operation part 207 has a grip 208, an input part 209, a proximal opening section 206*b* of the channel 206, and a universal cord 210. The grip 208 is an area gripped by the operator. The input part 209 receives an operation input to curve the bending part 204. The universal cord 210 outputs the image imaged by the imaging part 203 to the outside. The universal cord 210 is connected to a display device such as a liquid crystal display or the like via an image processing device including a processor or the like.

[Treatment Tool 100]

Figure 2:
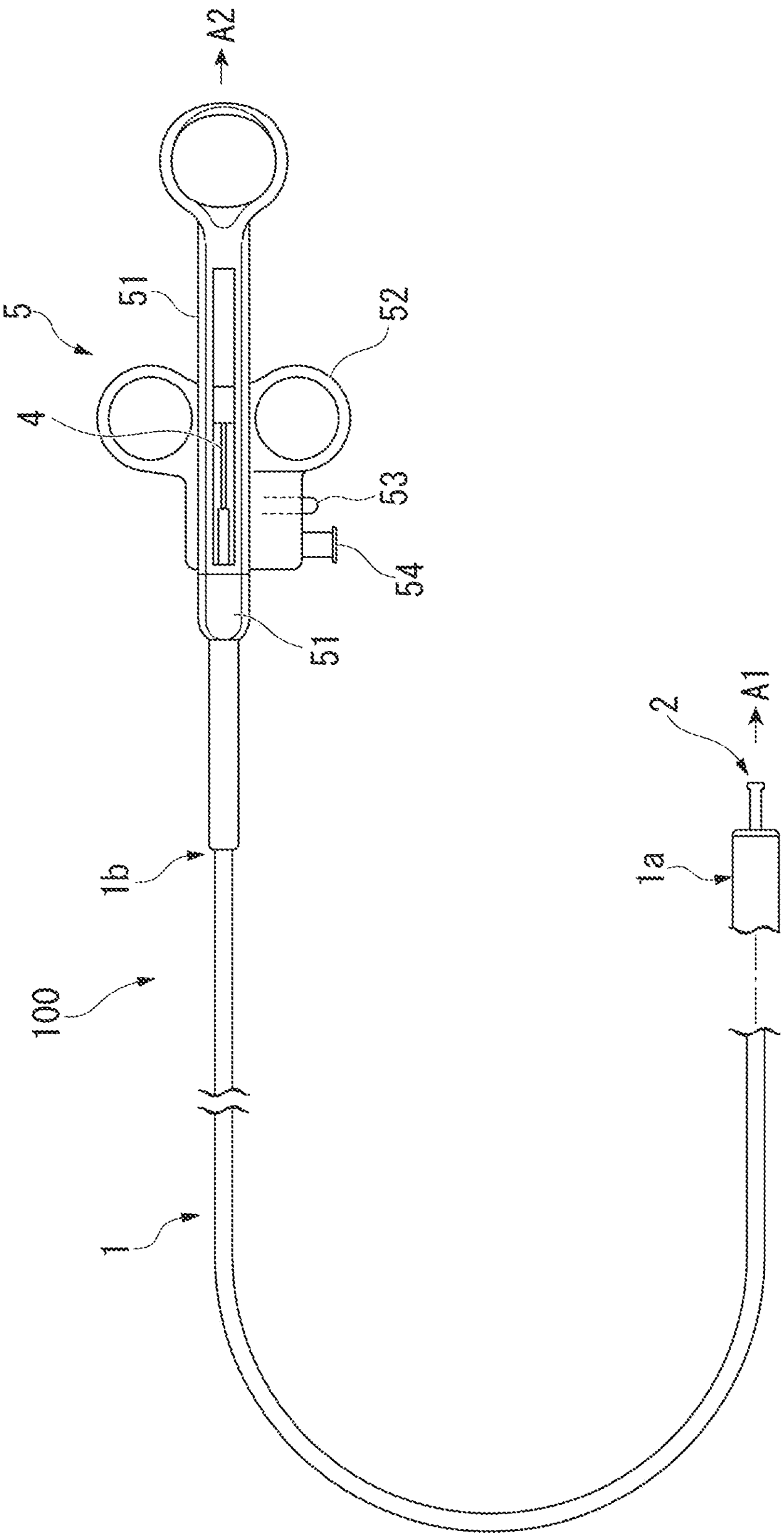
FIG. 2 is an overall view of a treatment tool of the endoscope treatment system according to the first embodiment.

FIG. 2 is an overall view of the treatment tool 100.

The treatment tool (treatment tool for an endoscope) 100 includes a sheath 1, the hollow pipe 2, an operation wire 4, and an operation part 5. In the following description, in a longitudinal direction A of the treatment tool 100, a side inserted into the body of the patient is referred to as "a distal side A1" and a side of the operation part 5 is referred to as "a proximal side A2." In FIG. 2, a distal part of the treatment tool 100 is shown as being enlarged.

The sheath 1 has flexibility and insulation. The sheath 1 is an elongated resin member and extending from a distal end 1*a* to a proximal end 1*b*. The sheath 1 has an outer diameter that enables insertion into the channel 206 of the endoscope 200 shown in FIG. 1. The sheath 1 is provided to be advancable and retractable in the channel 206. As shown in FIG. 1, in a state in which the sheath 1 is inserted into the channel 206, the distal end 1*a* of the sheath 1 is configured to protrude from and retract to the distal opening section 206*a* of the channel 206.

Figure 3:
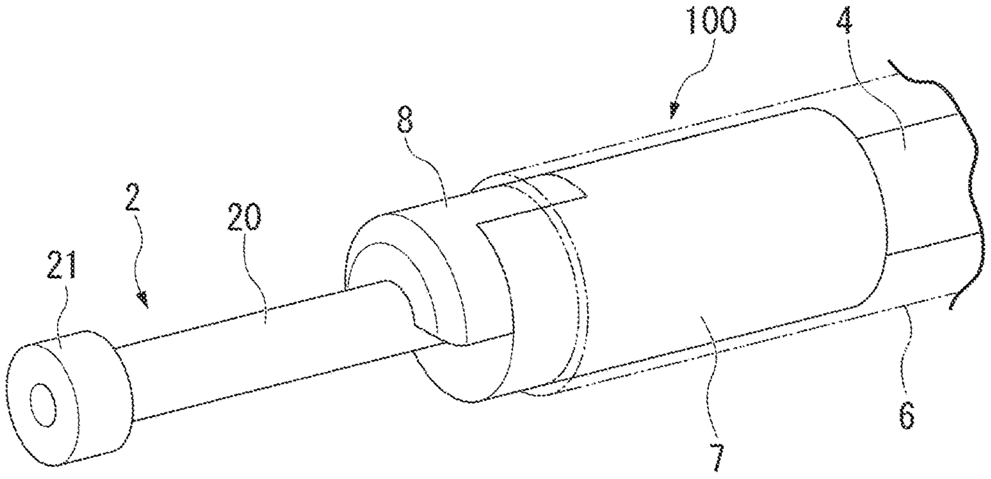
FIG. 3 is a perspective view of a distal end portion of the treatment tool according to the first embodiment.
Figure 4:
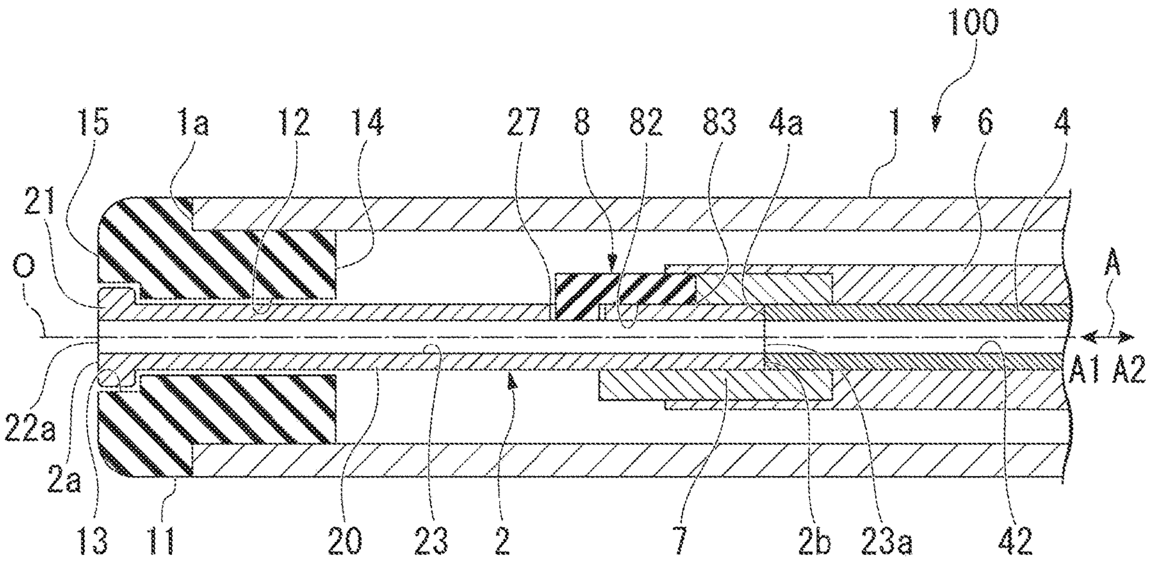
FIG. 4 is a cross-sectional view of the distal end portion of the treatment tool according to the first embodiment.
Figure 5:
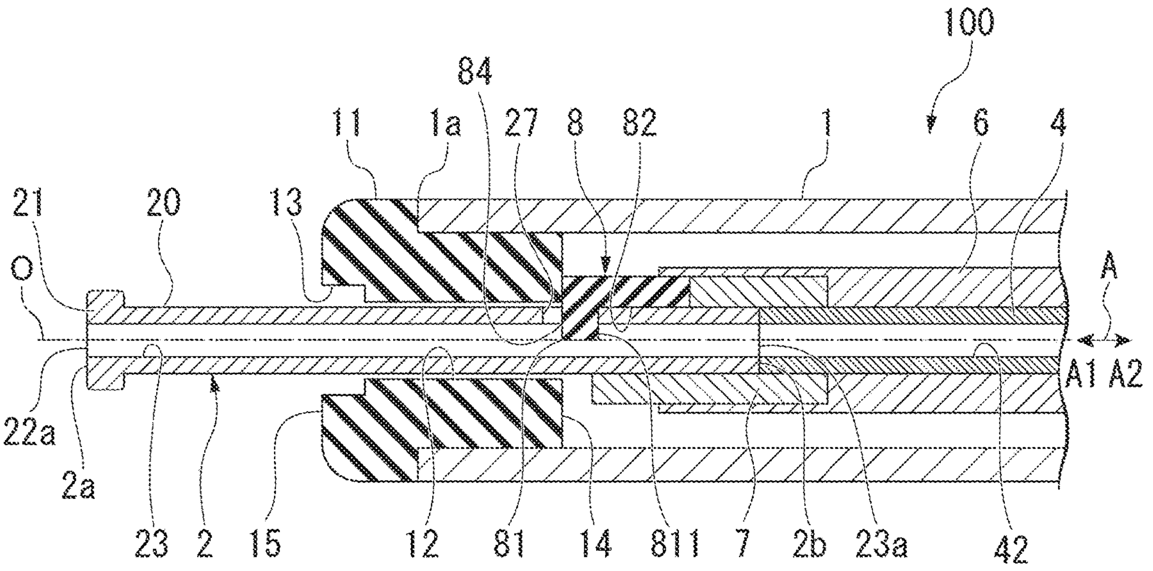
FIG. 5 is a cross-sectional view of the distal end portion of the treatment tool according to the first embodiment.

FIG. 3 is a perspective view of a distal end portion of the treatment tool 100. FIG. 4 and FIG. 5 are cross-sectional views of the distal end portion of the treatment tool 100. As shown in FIG. 4, a pipe holder (a pipe holding member) 11 having a through-hole 12 passing in the longitudinal direction A is attached to the distal end 1*a* of the sheath 1. The pipe holder 11 is formed of an insulating material. A stepped portion 13 is formed in a circumferential edge portion of the through-hole 12 in a distal end surface 15 of the pipe holder 11. The stepped portion 13 is a concave portion with a size into which a flange 21 of the hollow pipe 2, which will be described below, is capable of being inserted. The hollow pipe 2 is inserted into the through-hole 12.

The hollow pipe 2 is a substantially round rod-shaped member formed of a metal. The hollow pipe 2 is formed of a metal material having electric conductivity such as stainless steel or the like. The hollow pipe 2 has electric conductivity. The hollow pipe 2 is a tubular member in which a flow channel 23 is formed in the longitudinal direction A. The flow channel 23 extends between a distal end 2*a* and a proximal end 2*b* of the hollow pipe 2. The hollow pipe 2 has a tube main body 20 and the flange 21. The flange 21 is provided on the distal end of the tube main body 20. The flange 21 has an annular shape with an outer diameter greater than that of the tube main body 20. In a front view when the flange 21 is seen in a direction along the longitudinal direction A, an outer circumference of the flange 21 is formed in a circular shape concentric with the outer circumference of the tube main body 20. A distal opening 22*a* that is a distal end of the flange 21 is opened. A side hole (an opening) 27 in communication with the flow channel 23 is formed in the tube main body 20 of the hollow pipe 2. The side hole 27 is partially open in a circumferential direction of the hollow pipe 2.

In the embodiment, while the flange 21 has been described as being an annular shape with an outer diameter greater than that of the tube main body 20, the flange 21 may be not only an annular shape but also a polygonal shape such as a triangular shape, a rectangular shape, or the like, or an elliptical shape.

The operation wire 4 is attached to a proximal end of the tube main body 20. The operation wire 4 is formed of a metal material having electric conductivity such as stainless steel or the like. A water supply pipeline 42 is formed in the operation wire 4 throughout the entire length. The operation wire 4 is, for example, a dense winding coil. The operation wire 4 is inserted through an internal space of the sheath 1.

The proximal end 2*b* of the hollow pipe 2 is connected to a distal end 4*a* of the operation wire 4. The proximal end 2*b* of the hollow pipe 2 and the distal end 4*a* of the operation wire 4 are connected by a connecting pipe 7. The proximal end 2*b* of the hollow pipe 2 and the distal end 4*a* of the operation wire 4 are disposed in the through-hole of the connecting pipe 7 in a state in which they are in contact with each other. The proximal end 2*b* of the hollow pipe 2 and the distal end 4*a* of the operation wire 4 are fixed to the connecting pipe 7. An opening 23*a* of the proximal end 2*b* of the tube main body 20 is connected to the operation wire 4. The water supply pipeline 42 is in communication with the proximal end of the flow channel 23 of the hollow pipe 2.

A constricting member 8 is attached to the connecting pipe 7. As shown in FIG. 3 to FIG. 5, the constricting member 8 is attached to a distal side of the connecting pipe 7. The constricting member 8 corresponds to an elastically deformable constricting member. The constricting member 8 has a semi-cylindrical shape in which a cylinder member is divided in the longitudinal direction A. The constricting member 8 has a contacting surface 82. The contacting surface 82 of the constricting member 8 is disposed to face an outer surface of the hollow pipe 2 and come into contact with the outer surface. The constricting member 8 includes a constricting part 81. The constricting part 81 corresponds to a first end of the constricting member 8. The constricting part 81 is a protrusion having a size such that the protrusion can enter the side hole 27 of the hollow pipe 2. The constricting part 81 extends to a distal side from the contacting surface 82 disposed along the outer surface of the hollow pipe 2. As shown in FIG. 5, the constricting part 81 has a constricting surface 811 extending in a direction crossing a center axis O of the hollow pipe 2 in the longitudinal direction A. In the embodiment, the constricting surface 811 is substantially perpendicular to the center axis O and directed toward the proximal side.

The constricting part 81 is disposed outside the flow channel 23 of the hollow pipe 2. Specifically, in a natural state in which an external force is not applied, the constricting part 81 is disposed at a position where it is flush with an inner circumferential surface of the flow channel 23 of the hollow pipe 2 or at a position of an outer side of the inner wall surface. At least the constricting part 81 in the constricting member 8 is configured to be elastically deformable. In the embodiment, the constricting member 8 is formed of an elastically deformable material as a whole.

The operation wire 4 is covered with a cover tube 6 having insulation throughout the entire length. A distal end portion of the cover tube 6 extends to the connecting pipe 7 and covers a proximal portion of the connecting pipe 7. A proximal end 83 of the constricting member 8 is covered with the distal end portion of the cover tube 6. The cover tube 6 is, for example, a heat shrinkable tube. A liquid does not leak from the water supply pipeline 42 of the operation wire 4 by covering the outer circumference of the operation wire 4 with the cover tube 6.

The tube main body 20 supplies the high frequency current supplied from the operation wire 4 connected to the operation part 5 to the flange 21. When the high frequency current is supplied from the operation wire 4 to the hollow pipe 2, the tube main body 20 and the flange 21 function as a monopolar electrode configured to output the high frequency current to the biological tissue.

The hollow pipe 2 is provided to be inserted into the through-hole 12 of the pipe holder 11 and able to advance and retract with respect to the sheath 1. The hollow pipe 2 is capable of protruding from the through-hole 12 of the pipe holder 11 toward the distal side A1. FIG. 4 is a cross-sectional view when the hollow pipe 2 is disposed at a position retracted most, and FIG. 5 is a cross-sectional view when the hollow pipe 2 is disposed at a position advanced most. The center axis O of the hollow pipe 2 in the longitudinal direction A substantially coincides with a center axis of the sheath 1 in the longitudinal direction A.

As shown in FIG. 1 and FIG. 2, the operation part 5 has an operation part main body 51, a slider 52, a power feed connector 53, and a liquid supply port 54. A distal end of the operation part main body 51 is connected to the proximal end 1*b* of the sheath 1. The operation part main body 51 has an internal space into which the operation wire 4 is capable of being inserted. The operation wire 4 passes through the internal space of the sheath 1 and the internal space of the operation part main body 51 and extends to the slider 52.

The slider 52 is attached to be movable with respect to the operation part main body 51 in the longitudinal direction A. The slider 52 is attached to the sheath 1 connected to the operation part main body 51 via an O-ring. A proximal end of the operation wire 4 is attached to the slider 52. When the operator operates the slider 52 to relatively advance and retract with respect to the operation part main body 51, the operation wire 4 and the hollow pipe 2 advance or retract.

The power feed connector 53 is fixed to the slider 52. The power feed connector 53 is connected to the proximal end of the operation wire 4 via a conductive wire (not shown). The power feed connector 53 is configured to be connected to a high frequency power supply device (not shown), and the high frequency current supplied from the high frequency power supply device is supplied to the hollow pipe 2 via the power feed connector 53 and the operation wire 4.

The liquid supply port 54 is provided in the slider 52. The liquid supply port 54 is in communication with the proximal end of the water supply pipeline 42 of the operation wire 4 via the water supply pipeline formed in the slider 52. The liquid supplied from the liquid supply port 54 passes through the water supply pipeline of the slider 52, the water supply pipeline 42 of the operation wire 4 and the flow channel 23 to be discharged from the distal opening 22*a* (shown in FIG. 5).

The operation wire 4 and the hollow pipe 2 advance and retract into the sheath 1 when the operator operates the slider 52 to relatively advance and retract with respect to the operation part main body 51. The hollow pipe 2 is capable of being accommodated in the stepped portion 13 of the pipe holder 11 upon retract. A length of the longitudinal direction A from the distal end portion of the hollow pipe 2 to the constricting member 8 is greater than the length of the pipe holder 11.

Figure 7:
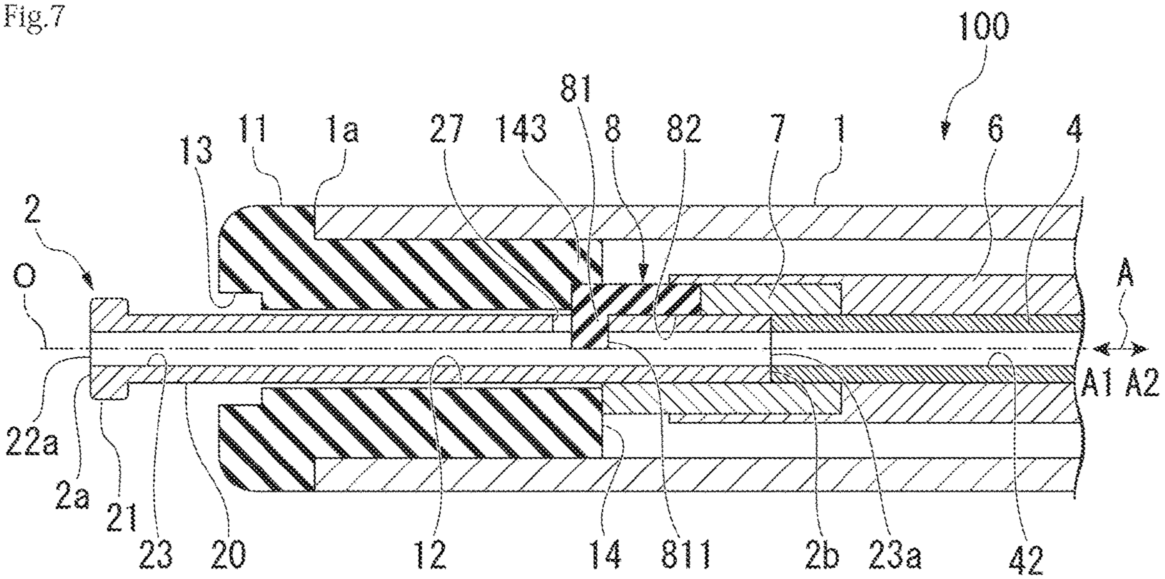
FIG. 7 is a cross-sectional view of a distal end portion of a treatment tool of a modified example of the first embodiment.

As shown in FIG. 7, when the slider 52 is further pressed at a position where the constricting member 8 comes into contact with the proximal end of the pipe holder 11, a force pressed toward the proximal side is applied to the constricting part 81. Here, the constricting member 8 is also pressed by the operation wire 4 on the distal side. As a result, the constricting part 81 is compressed and deformed in the longitudinal direction A, and the constricting part 81 deforms to extend in a direction crossing the longitudinal direction A. As a result, the constricting part 81 protrudes from the side hole 27 into the flow channel 23 to narrow the flow channel 23. That is, the constricting part 81 protrudes into the flow channel 23, and the constricting surface 811 narrows a part of the flow channel 23. As a result, the flow channel 23 is partially occluded by protrusion of the constricting part 81, and an opening area is narrowed. The flow channel 23 is narrowed once by the constricting part 81. The water pressure (water supply pressure) is increased as the liquid supplied to the flow channel 23 of the hollow pipe 2 passes through a place narrowed by the constricting part 81. The liquid with the increased water pressure is supplied from the distal opening 22*a*. As a result, a water force of the liquid can be increased in the flow channel 23, and the liquid can be supplied in a state in which the water force is strengthened from the distal opening 22*a*. For example, even when the water pressure of the liquid passing through the water supply pipeline of the slider 52 and the water supply pipeline 42 of the operation wire 4 is lowered, the water force can be increased in the flow channel 23 of the hollow pipe 2, and the liquid can be supplied in a state in which the water force is strengthened from the distal opening 22*a*.

While the example in which the constricting surface 811 is substantially perpendicular to the center axis O and directed toward the proximal side has been shown in the embodiment, the orientation of the constricting surface 811 is not limited to the example. The constricting surface 811 may be configured to narrow a part of a flow of the fluid in the flow channel 23, and the constricting surface 811 may be inclined in a direction crossing the longitudinal direction A.

When the slider 52 is retracted and the operation wire 4 and the hollow pipe 2 are retracted with respect to the sheath 1, the constricting member 8 is separated from the pipe holder 11. Accordingly, the constricting member 8 returns to a natural state in which an external force is not applied to the constricting member 8, and compression of the constricting part 81 is released. When the compression of the constricting part 81 is released, the constricting part 81 returns to a state substantially flush with the inner wall of the flow channel 23 as shown in FIG. 4 from a state protruding into the flow channel 23 as shown in FIG. 5. That is, when a relative position of the hollow pipe 2 with respect to the sheath 1 is displaced, the constricting part 81 protrudes from and retracts into the side hole 27 with respect to the flow channel 23. A type in which the constricting part 81 is positioned on an inner side of the inner circumferential surface of the flow channel 23 in the radial direction and the flow channel 232 is narrowed as the tip of the constricting part 81 protrudes from the side hole 27 into the flow channel 23 is referred to as a high water pressure configuration. The high water pressure configuration corresponds to a first position of the hollow pipe 2 relative to the sheath 1. A type in which the constricting part 81 is flush with the inner circumferential surface of the flow channel 23 and located on an outer side of the inner circumferential surface in the radial direction is referred to as a low water pressure configuration. The low water pressure configuration corresponds to a second position of the hollow pipe 2 relative to the sheath 1. The constricting member 8 configures the low water pressure configuration in a natural state in which an external force is not applied, and the constricting part 81 is deformed from the low water pressure configuration by the application of the external force to configure the high water pressure configuration. In the first position, a cross-section of the flow channel 23 has a first area at a position. The first end of the elastically deformable constricting member is inserted at the position. In the second position, the cross-section of the flow channel has a second area at the position. The first end of the elastically deformable constricting member is inserted. The first area is less than the second area.

[Method for Using Treatment Tool for Endoscope]

Next, an example of method for using the treatment tool 100 for an endoscope according to the embodiment will be described. Specifically, local injection treatment, incision-peeling treatment and hemostasis treatment of a lesioned part in endoscopic treatment such as endoscopic submucosal dissection (ESD) or the like will be described. The operator specifies a lesioned part using a known method. For example, the operator inserts the insertion part 202 of the endoscope 200 into the digestive canal (for example, the gullet, the stomach, the duodenum, the large intestine), and specifies the lesioned part while observing the image obtained by the imaging part 203 of the endoscope.

Next, the operator inserts the treatment tool 100 into the channel 206, and causes the distal end 1*a* of the sheath 1 to protrude from the distal opening section 206*a* of the insertion part 202. The operator causes the slider 52 of the operation part 5 to relatively advance with respect to the operation part main body 51 and causes the hollow pipe 2 to protrude from the distal end 1*a* of the sheath 1 toward the distal side.

The operator performs an operation of moving the slider 52 toward the distal side A1 with respect to the operation part main body 51, and moves the hollow pipe 2 toward the distal side A1. As a result, the flange 21 of the hollow pipe 2 protrudes toward the distal side A1 with respect to the sheath 1. Here, when the slider 52 is pushed toward the distal side, and as shown in FIG. 4, when the operation wire 4 and the hollow pipe 2 advance with respect to the sheath 1, the operation wire 4 and the hollow pipe 2 advance to a position where a distal end 84 of the constricting member 8 abuts a proximal end surface 14 (a proximal end wall) of the pipe holder 11. The operation wire 4 and the hollow pipe 2 can advance and retract from a position where the flange 21 is accommodated in the stepped portion 13 to a position where the constricting member 8 comes into contact with the proximal end surface 14 of the pipe holder 11.

The operator pushes the distal end of the hollow pipe 2 against the lesioned part into which a liquid for local injection (local injection liquid) is injected, and supplies water in a state in which the distal opening 22*a* is pushed against the tissue (a local injection step). When the hollow pipe 2 is pushed against the lesioned part, the hollow pipe 2 protrudes most, the constricting member 8 comes into contact with the proximal end surface 14 of the pipe holder 11, and thus, the constricting part 81 is pressed. As a result, the constricting part 81 protrudes into the flow channel 23. In this state, the liquid such as a physiological saline solution or the like is supplied from the liquid supply port 54 to the water supply pipeline 42 of the slider 52. The liquid passes through the water supply pipeline 42 of the operation wire 4 and the flow channel 23 and is supplied (discharged) from the distal opening 22*a* toward the distal side. The flow channel 23 has an opening area reduced at a position of the constricting part 81. Accordingly, the liquid supplied to the flow channel 23 passes through the place where the flow channel is narrowed by the constricting part 81 that was protruded, and thus, the water force is strengthened. Accordingly, the liquid can be supplied from the distal opening 22*a* in a state in which the water force is strong. As a result, the liquid with the strong water force can be supplied to inflate the lesioned part in a state in which the distal opening 22*a* is pushed against the mucous membrane of the lesioned part. In the local injection treatment for inflating the lesioned part before incision, the local injection may be performed by punching the lesioned part with the hollow needle using a known local injection device.

After the lesioned part is inflated, the operator performs incision and peeling treatment (incision peeling step). Electrical conduction by the high frequency current to the hollow pipe 2 is performed from the high frequency power supply device (not shown) connected to the power feed connector 53 of the operation part 5 through the power feed connector 53 and the operation wire 4. The flange 21 of the conducted hollow pipe 2 functions as a high frequency knife. For example, the operator moves the flange 21 in a lateral direction perpendicular to a longitudinal axis C, and the mucous membrane (tissue) in contact with the flange 21 is incised. After the lesioned mucous membrane portion is completely incised in the circumferential direction, the flange 21 abuts a slit where a periphery of the lesioned mucous membrane portion is incised, and the lesioned mucous membrane portion is entirely incised and peeled. In addition, the operator peels the submucosa of the incised lesioned part while lifting the mucous membrane of the incised lesioned part and exposing the submucosa in a state in which the treatment tool 100 advances and the high frequency current is applied.

The operator can perform additional local injection treatment. The operator causes the hollow pipe 2 to protrude toward the distal side A1 most. The operator pushes the flange 21 against an area where the local injection liquid is additionally injected, and the liquid is supplied from the distal opening 22*a* (additional local injection step). As described above, when the hollow pipe 2 protrudes most and the constricting member 8 comes into contact with the proximal end surface 14 of the pipe holder 11 to press the constricting part 81, the constricting part 81 protrudes into the flow channel 23. The flow channel 23 has an opening area reduced at a position of the constricting part 81. The liquid supplied to the water supply pipeline of the slider 52, the water supply pipeline 42 of the operation wire 4 and the flow channel 23 from the liquid supply port 54 in this state passes through a place where the flow channel is narrowed by the protruded constricting part 81, and thus, the water force is strengthened. Accordingly, the liquid supplied to the flow channel 23 can be supplied from the distal opening 22*a* in a state in which the water force is strengthened. The distal opening 22*a* abuts the mucous membrane of the lesioned part to push the flange 21, and additional local injection can be performed on the lesioned part when the liquid is supplied in a state in which the water force is strengthened.

When bleeding occurs during the incision and peeling treatment, the operator performs hemostasis treatment. The operator cauterizes the bleeding point to perform hemostasis while pressing the flange 21 that has become hot due to conduction by the high frequency current (hemostasis step).

The operator can clean the operation site in cleaning step. Here, the hollow pipe 2 is at the position where the hollow pipe 2 is retracted in comparison with the time of the local injection step and the incision peeling step. Specifically, in a state in which the constricting member 8 is disposed at a position separated from the proximal end surface 14 of the pipe holder 11 toward the proximal side A2, a liquid such as a physiological saline solution or the like is supplied. The constricting member 8 is in the natural state in which the external force is not applied at a position where the constricting member 8 is separated from the proximal end surface 14 of the pipe holder 11. When the constricting member 8 is in the natural state, for example, the constricting part 81 is to be flush with the inner surface of the flow channel 23 of the tube main body 20. Alternatively, the constricting part 81 is located in the side hole 27 on the outer side of the inner surface of the flow channel 23 in the radial direction. That is, the constricting part 81 is disposed at a position that does not interfere with the flow channel 23. In this state, the liquid can be supplied in the hollow pipe 2 in a state in which the water force is lower than upon the local injection. During the operation site cleaning, the liquid is supplied at a position where the flange 21 is separated from the tissue. When the liquid is supplied in a state in which the water force is high upon local injection at a position where the flange 21 is separated from the tissue, bubbles are generated, the liquid splashes from the cleaning target area, and a field of vision of the imaging part 203 of the endoscope is reduced, which interferes with the treatment. However, when the constricting part 81 is disposed at a position that does not interfere with the flow channel 23, the water force becomes weaker than that upon local injection, and the cleaning is performed favorably. Upon the operation site cleaning, the constricting part 81 may be positioned on the proximal side of the hollow pipe 2 separated from the proximal end surface 14.

The operator can continue the above-mentioned operation (treatment), incise the lesioned part finally, and terminate the ESD procedure.

According to the treatment tool 100 of the embodiment, a plurality of treatments such as local injection treatment, incision peeling treatment, hemostasis treatment, additional local injection, operation site cleaning, and the like, can be performed. According to the treatment tool 100 of the embodiment, a plurality of treatments such as local injection treatment, incision peeling treatment, hemostasis treatment, additional local injection, operation site cleaning, and the like, can be performed without inserting and removing the treatment tool 100 into/from the channel 206 of the endoscope 200.

Hereinabove, while the first embodiment of the present disclosure has been described in detail with reference to the accompanying drawings, a specific configuration is not limited to the embodiment and also includes design changes or the like without departing from the spirit of the present disclosure. In addition, the components shown in the above-mentioned embodiment and modified examples may be combined appropriately. In the following description, the common components as those as already described are designated by the same reference signs and overlapping description will be omitted.

The constricting member 8 is not limited to a substantially semi-cylindrical shape. For example, the constricting member 8 may have an elongated shape extending in the longitudinal direction A to cover a region on the proximal side of the side hole 27 and the side hole 27.

Modified Example 1-1

Figure 6:
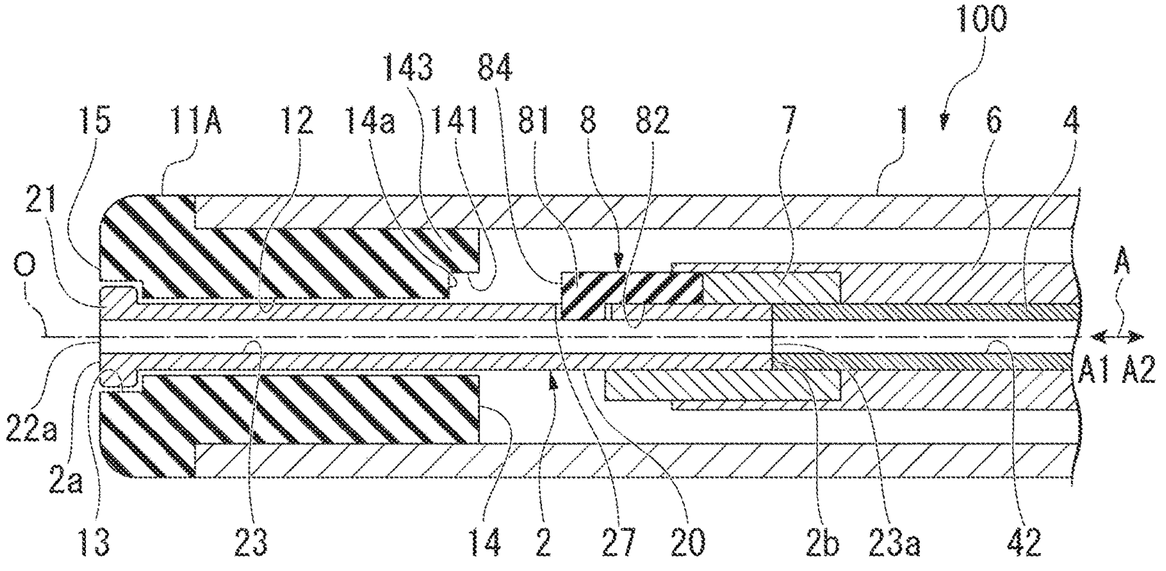
FIG. 6 is a cross-sectional view of a distal end portion of a treatment tool of a modified example of the first embodiment.

A modified example of the embodiment will be described with reference to FIG. 6 and FIG. 7. As shown in FIG. 6 and FIG. 7, a concave portion 141 may be formed in the proximal end surface 14 of the pipe holder 11. The concave portion 141 is recessed from the proximal end surface 14 toward the distal side in a boundary portion between the proximal end surface 14 and the through-hole 12. The concave portion 141 is an opening having a size into which the distal end portion of the constricting member 8 can enter. Specifically, the concave portion 141 is an opening having a size that comes into contact with the constricting member 8 when the distal end portion of the constricting member 8 intrudes thereinto. In the concave portion 141, a surface 14*a* positioned on the distal side perpendicular to the longitudinal axis of the through-hole 12 constitutes the proximal end surface 14*a*. A portion 143 on an outer side of the concave portion 141 in the radial direction constitutes a restriction part 143 protruding toward the proximal side A2 of the longitudinal axis of the through-hole. The restriction part 143 corresponds to a protrusion. As shown in FIG. 7, the operation wire 4 and the hollow pipe 2 advance, and the distal end 84 of the constricting member 8 enters the concave portion 141 and comes in contact therewith. When the operation wire 4 is pressed at the distal side A1 in a state in which the distal end portion of the constricting member 8 enters the concave portion 141, the distal end 84 comes into contact with the proximal end surface 14*a* to apply an external force to the constricting part 81 and compress the constricting part 81. Since an outer circumferential portion of the constricting member 8 is disposed in the concave portion 141 and covered with the restriction part 143, the compression force of the constricting part 81 is applied toward the center axis O. As a result, the compressed constricting part 81 protrudes from an outer side of the tube main body 20 into the flow channel 23. Accordingly, the compressed constricting part 81 can smoothly protrude into the flow channel 23. In addition, since the compressed constricting part 81 protrudes into the flow channel 23 in the radial direction, the constricting surface 811 tends to be oriented in a direction substantially perpendicular to the center axis O. As a result, the opening area of the flow channel 23 can be more reliably narrowed, and switching of the water force of the flow channel 23 by the constricting part 81 is reliably performed. Accordingly, the treatment tool 100 is configured to be easily change the water force of the liquid supplied from the distal opening 22*a*.

Modified Example 1-2

Figure 8:
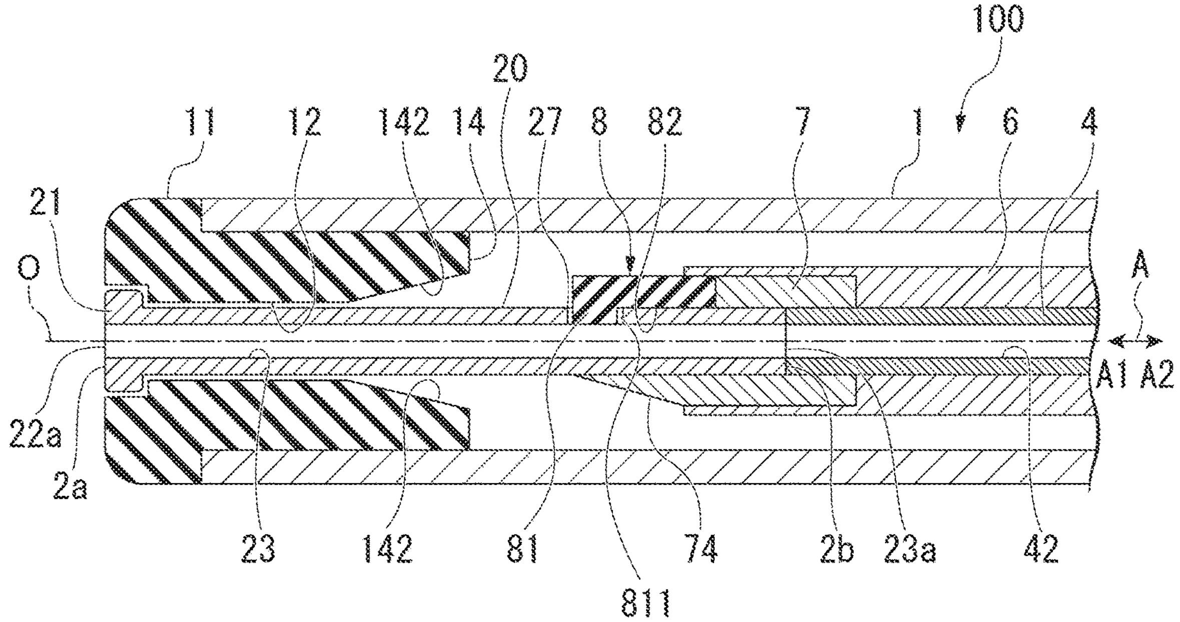
FIG. 8 is a cross-sectional view of a distal end portion of a treatment tool of a modified example of the first embodiment.
Figure 9:
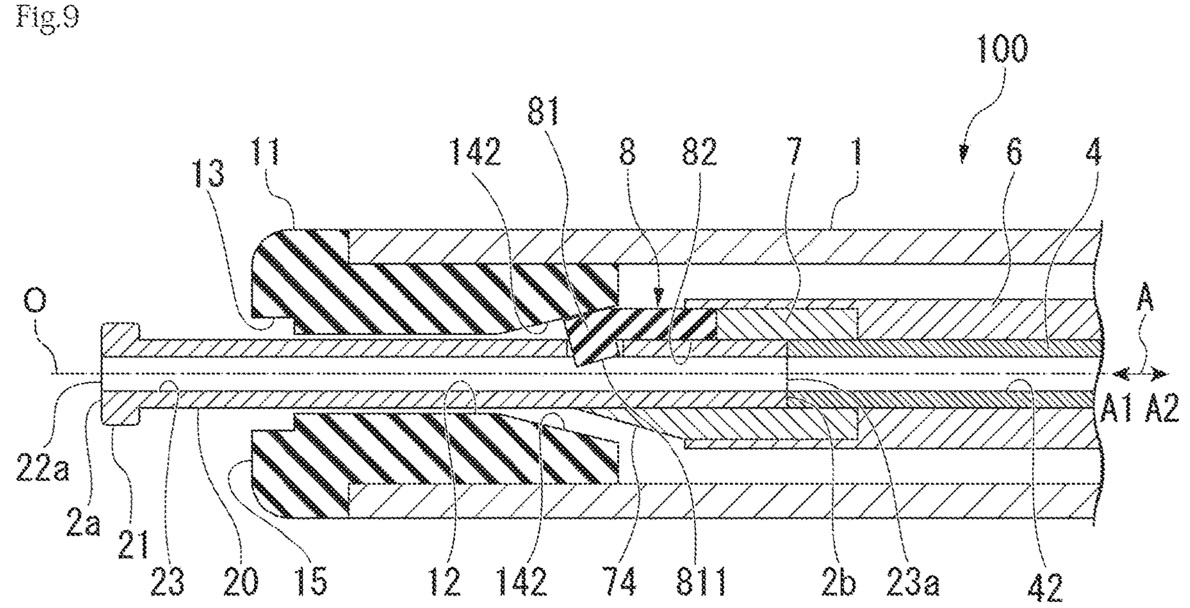
FIG. 9 is a cross-sectional view of a distal end portion of a treatment tool of a modified example of the first embodiment.

A modified example of the embodiment will be described with reference to FIG. 8 and FIG. 9. The concave portion 141 may have a shape in which the constricting member 8 is inserted and the constricting part 81 can enter the flow channel 23, and is not limited to the shape shown in FIG. 6. As shown in FIG. 8 and FIG. 9, a concave portion 142 may have a tapered shape. The concave portion 142 has a tapered surface (inclined surface) formed such that the opening area is reduced from the proximal end surface 14 of the pipe holder 11 toward the distal side. The opening of the proximal end portion of the concave portion 142 has a size such that the distal end portion of the constricting member 8 can be entered.

As shown in FIG. 9, the operation wire 4 and the hollow pipe 2 advance, and the distal end 84 of the constricting member 8 enters the concave portion 142 and comes into contact therewith. When the operation wire 4 is pressed on the distal side A1 in a state in which the distal end portion of the constricting member 8 enters the concave portion 142, an external force is applied to the constricting part 81 to compress the constricting part 81. When the hollow pipe 2 advances, an outer circumferential edge 841 of the distal end 84 of the constricting part 81 is pressed along the tapered surface while coming into contact with the concave portion 142, and the constricting part 81 is elastically deformed to protrude into the flow channel 23. As a result, the constricting part 81 can smoothly protrude into the flow channel 23 in accordance with the operation of advancing the operation wire 4 and the hollow pipe 2. In the modified example, the inner circumferential surface of the constricting part 81 functions as the constricting surface 811. As a result, the constricting part 81 can smoothly protrude into the flow channel 23, and the opening area of the flow channel 23 can be more reliably narrowed. Meanwhile, the constricting part 81 gradually returns to its original position where it does not protrude into the flow channel 23 in accordance with the operation of retracting the operation wire 4 and the hollow pipe 2. As a result, switching of the water force of the flow channel 23 is reliably performed. Accordingly, the treatment tool 100 is configured to be easily change the water force of the liquid supplied from the distal opening 22*a*.

In the distal end portion of the connecting pipe 7, a portion facing the constricting member 8 with the center axis sandwiched therebetween has a tapered surface 74. The tapered surface 74 of the connecting pipe 7 is inclined to reduce a diameter toward the distal end portion. The tapered surface 74 is inclined not to come into contact with the concave portion 142 before the distal end of the constricting member 8 comes into contact with the concave portion 142. Accordingly, the contact of the constricting part 81 with the concave portion 142 is not prevented by the connecting pipe 7. The tapered surface 74 of the connecting pipe 7 is not a required configuration. As described above, the connecting pipe 7 may have a shape without interfering with the contact of the constricting part 81 with the concave portion 142.

In this example shown in FIG. 8 and FIG. 9, while the example of the concave portion 142 having a substantially conical opening formed coaxially with the through-hole 12 and a tapered surface has been shown, the concave portion 142 is not limited to the shape. For example, the concave portion 142 may be formed at only a position facing the constricting member 8, and a tapered surface may be formed on the concave portion 142. The concave portion 141 may be formed in the proximal end surface 14 of the pipe holder 11.

Modified Example 1-3

A modified example of the embodiment will be described with reference to FIG. 10 and FIG. 11. The constricting member 8 of the modified example shown in FIG. 8 and FIG. 9 may further include a slit 86. The slit 86 is located on the distal side of the contacting surface 82 to the hollow pipe 2 in the longitudinal direction A. The slit 86 is formed in a direction substantially perpendicular to the longitudinal direction A from an outer surface 85 of the constricting member 8. A position of the slit 86 in the longitudinal direction A overlaps a proximal edge 271 of the side hole 27 of the hollow pipe 2 or is provided on the distal side A1 other than the proximal edge 271. As shown in FIG. 11, the operation wire 4 and the hollow pipe 2 advance, and the outer circumferential edge 841 of the distal end 84 of the constricting member 8 enters the concave portion 142 and comes into contact therewith. When the operation wire 4 is pressed on the distal side A1 in a state in which the distal end portion of the constricting member 8 enters the concave portion 142, an external force is added to the constricting part 81, and the constricting part 81 electrically deforms using the slit 86 as an origin. The constricting part 81 is guided to the inclination of the concave portion 142 and protrudes from the outside of the tube main body 20 into the flow channel 23. As a result, the compressed constricting part 81 can smoothly protrude in the flow channel 23. As a result, the opening area of the flow channel 23 can be more reliably narrowed, and switching of the water force of the flow channel 23 by the constricting part 81 is reliably performed. Accordingly, the treatment tool 100 is changed between the low water pressure configuration and the high water pressure configuration in accordance with relative movement of the hollow pipe 2 with respect to the sheath 1, and is configured to be easily change the water force of the liquid supplied from the distal opening 22*a*.

Modified Example 1-4

Figure 12:
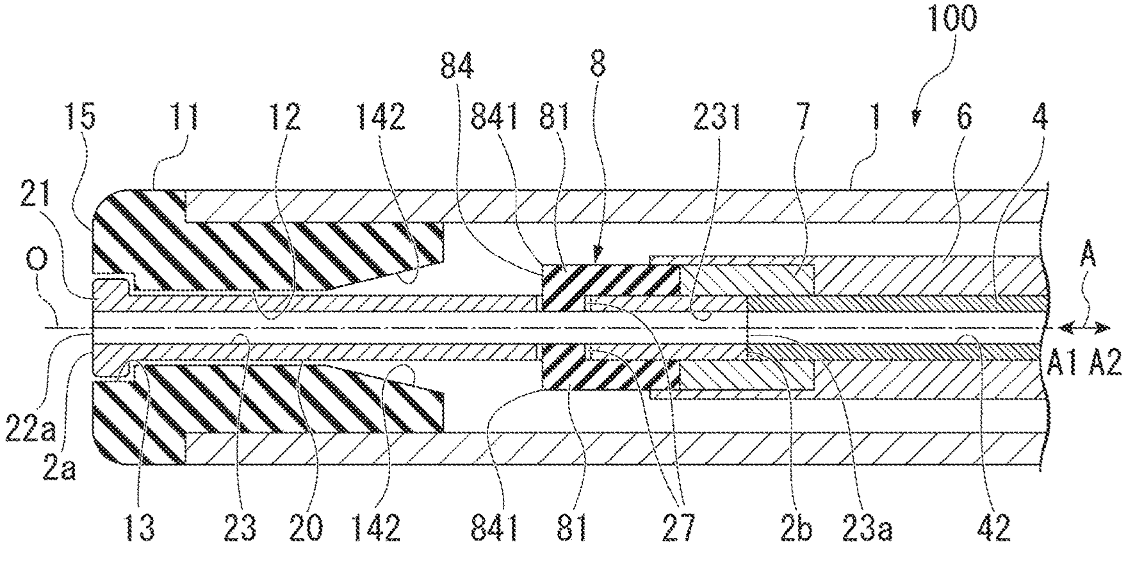
FIG. 12 is a cross-sectional view of a distal end portion of a treatment tool of a modified example of the first embodiment.
Figure 13:
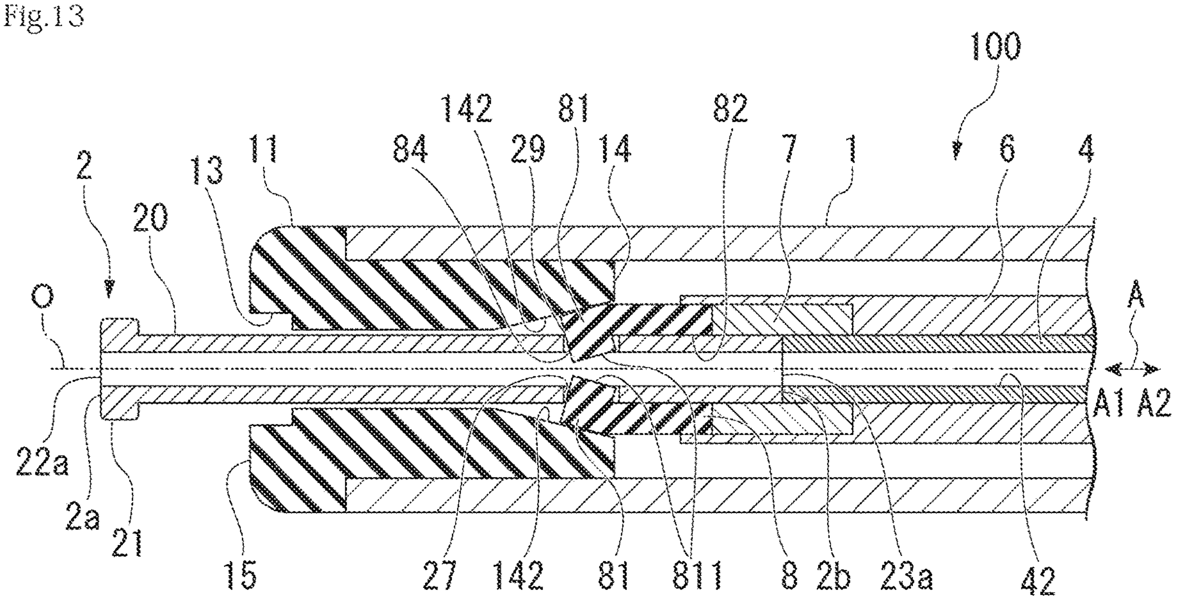
FIG. 13 is a cross-sectional view of a distal end portion of a treatment tool of a modified example of the first embodiment.

In the embodiment and modified example, while the example in which the side hole 27 is opened at one place in the circumferential direction of the hollow pipe 2 and the constricting part 81 protrudes and retracts into the flow channel 23 has been shown, each of the number of the constricting part 81 and the side hole 27 is not limited to one and may be provided in plural. As shown in FIG. 12 and FIG. 13, the treatment tool 100 may include the pair of side holes 27 and the pair of constricting parts 81 at facing positions with the center axis O of the hollow pipe 2 sandwiched therebetween. As shown in FIG. 13, the operation wire 4 and the hollow pipe 2 advance, and the outer circumferential edge 841 of the distal end 84 of the constricting member 8 enters the concave portion 142 and comes into contact therewith. When the operation wire 4 is pushed on the distal side A1 in a state in which the distal end portion of the constricting member 8 enters the concave portion 142, an external force is added to the constricting part 81, the pair of constricting parts 81 are guided to the inclination of the concave portion 142, and the distal end portion protrudes from an outer side of the tube main body 20 into the flow channel 23. In the case of the example, a surface of the constricting part 81 in the longitudinal direction A functions as the constricting surface 811. According to the treatment tool 100 of the example, the pair of constricting parts 81 can smoothly protrude in the flow channel 23. As a result, the opening area of the flow channel 23 can be more reliably narrowed, and switching of the water force of the flow channel 23 by the constricting part 81 is reliably performed. Accordingly, the treatment tool 100 is configured to be easily change the water force of the liquid supplied from the distal opening 22*a*. A difference between a place where the opening area of the flow channel 23 is wide and a place where the opening area is narrow can be increased and the liquid can be supplied in a state in which the water force is higher in accordance with the configuration in which the pair of constricting parts 81 advance and retract into the flow channel 23. Meanwhile, when the operation wire 4 and the hollow pipe 2 retract, the pair of constricting parts 81 are moved outward in the radial direction and changed in a state in which the constricting part 81 does not interfere with the flow channel 23. Accordingly, the water force of the liquid supplied from the distal opening 22*a* can be greatly changed. While not shown, each of the constricting parts in the example may include the slit 86 shown in FIG. 10 and FIG. 11.

According to the treatment tool 100 of the embodiment and modified example, the constricting part 81 can protrude and retract with respect to the flow channel 23 and the opening area of the flow channel 23 can be changed in accordance with the operation of causing the operation wire 4 and the hollow pipe 2 to advance and retract with respect to the sheath 1. That is, by operating the slider 52 of the operation part 5 to advance and retract, the opening area of the flow channel 23 can be changed, and the water force of the liquid supplied from the distal opening 22*a* via the flow channel 23 can be changed. Accordingly, for example, the liquid can be supplied from the distal opening 22*a* in a state in which the water force is high at the time of the local injection and re-local injection, and the liquid can be supplied from the distal opening 22*a* in a state in which the water force is low at the time of the operation site cleaning.

Second Embodiment

A treatment tool 100B according to a second embodiment will be described with reference to FIG. 14 to FIG. 16. In the following description, the same components as described above are designated by the same reference signs and overlapping descriptions thereof will be omitted.

Figure 14:
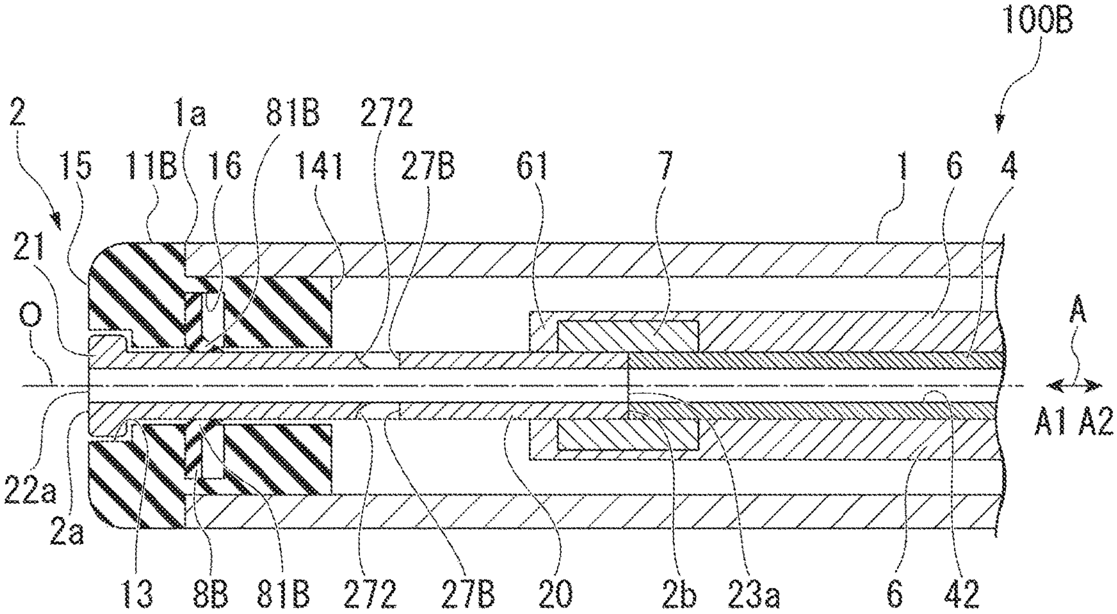
FIG. 14 is a cross-sectional view of a distal end portion of a treatment tool of a second embodiment.
Figure 15:
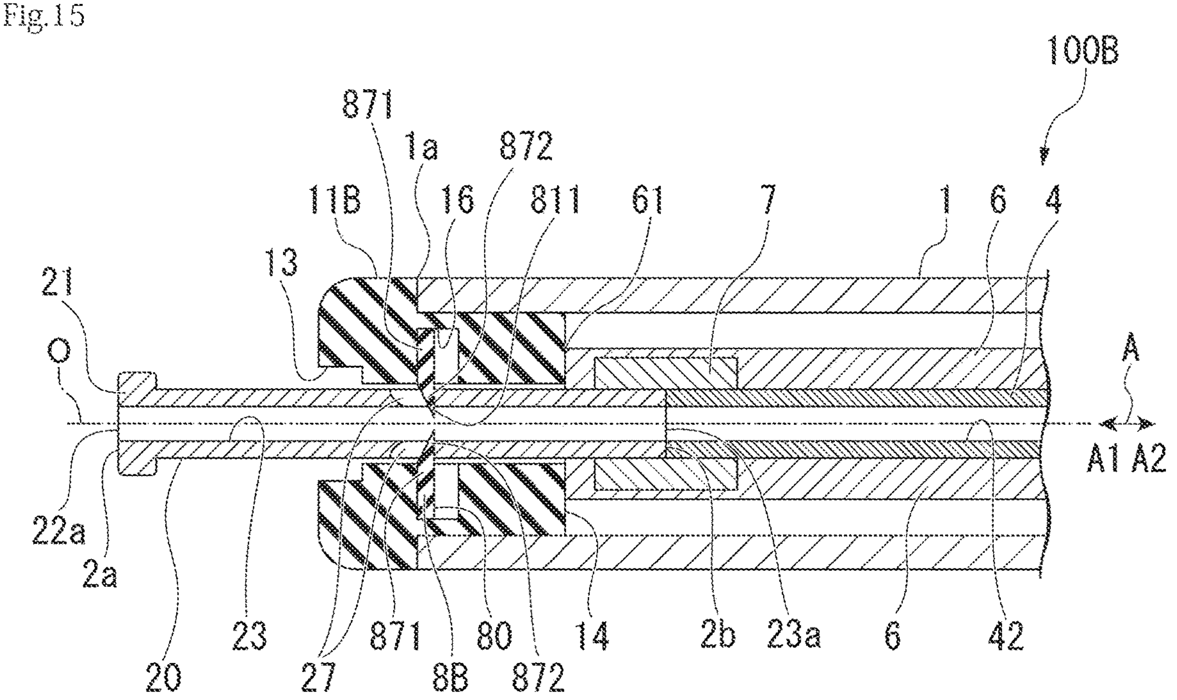
FIG. 15 is a cross-sectional view of the distal end portion of the treatment tool of the second embodiment.

FIG. 14 and FIG. 15 are cross-sectional views showing a distal end portion of the treatment tool 100B.

Like the treatment tool 100 of the first embodiment, the treatment tool (treatment tool for an endoscope) 100B configures an endoscope treatment system together with the endoscope 200. The treatment tool 100B includes a sheath 1, a hollow pipe 2, a pipe holder 11B, a constricting member 8B, an operation wire 4, a connecting pipe 7B, and an operation part 5.

In the embodiment, the constricting member 8 is provided on the pipe holder 11B. An accommodating section 16 (concave portion) in which the constricting member 8B is accommodated is formed in an intermediate section of the pipe holder 11B in the longitudinal direction A. The accommodating section 16 is an opening that is opened in the through-hole 12 and recessed from the through-hole 12 toward the outer circumference of the pipe holder 11B in the radial direction. In the embodiment, the accommodating section 16 is a circular opening.

The hollow pipe 2 has the side holes 27 formed at two places separated in the circumferential direction of the tube main body 20. In this example shown in FIG. 14 and FIG. 15, the two side holes 27 are open at positions separated 180 degrees in the circumferential direction. As shown in FIG. 14, the side hole 27B has a distal edge 272 that is inclined. Specifically, the distal edge 272 of the side hole 27B is inclined such that an edge portion in the outer surface of the hollow pipe 2 is located on the distal side of the edge portion in the inner surface of the flow channel 23.

Like the first embodiment, the proximal end of the hollow pipe 2 and the distal end of the operation wire 4 are connected by the connecting pipe 7. The connecting pipe 7 is entirely covered with the cover tube 6. A distal end 61 of the cover tube 6 comes into contact with an outer surface of the hollow pipe 2 that covers the distal part of the connecting pipe 7. The side hole 27 is located on a distal side of the cover tube 6.

Figure 16:
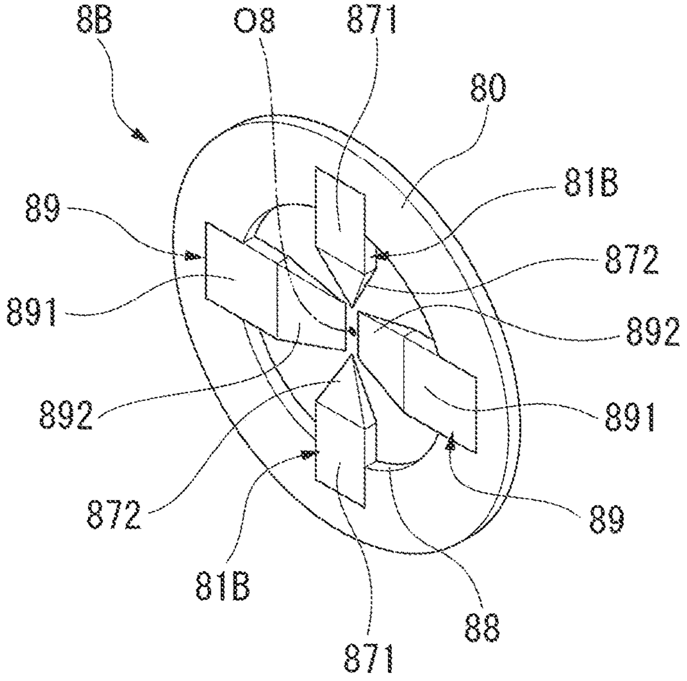
FIG. 16 is a perspective view of a constricting member of the second embodiment.

FIG. 16 is a perspective view of the constricting member 8B of the embodiment. The constricting member 8B has a main body 80, a constricting part 81B, and a holding part 89. The main body 80 has a substantially annular shape in which an opening 88 is formed in a central portion. The constricting part 81B is a protrusion extending from the main body 80 toward a center O8 of the opening 88 in the radial direction. The constricting part 81B has a base part 871 and a constricting piece 872 from the opening 88 in the radial direction. The base part 871 is a columnar part extending from the opening 88 in the radial direction. The constricting piece 872 has a square pyramid shape that is tapered from the base part 871 toward the center O8 of the opening 88. The constricting piece 872 is configured to be softer than the base part 871 and elastically deformable when an external force is applied. The constricting part 81B is provided to protrude from each of the positions separated 180 degrees in the circumferential direction of the main body 80. The pair of holding parts 89 are provided between the pair of constricting parts 81B, respectively. The holding part 89 has a holding base part 891 and a holding piece 892. The holding base part 891 is a columnar part extending from the opening 88 in the radial direction. The holding piece 892 has a shape in which a thickness in the longitudinal direction A is reduced from the holding base part 891 toward the center O8 of the opening 88. A projection end of the constricting piece 872 has a tip shape, and a projection end of the holding piece 892 has a long side. The holding piece 892 is configured to be softer than the holding base part 891 and elastically deformable when an external force is applied. The constricting member 8B is a part integrally formed of, for example, an elastic resin, a hard rubber, or the like.

As shown in FIG. 14 and FIG. 15, the constricting member 8B is disposed in the accommodating section 16 of the pipe holder 11B. An opening dimension of the accommodating section 16 in the radial direction has a size such that the main body 80 of the constricting member 8B is accommodated in the accommodating section 16 while an outer diameter of the main body 80 of the constricting member 8B comes in contact therewith. An opening dimension of the accommodating section 16 in the longitudinal direction A is greater than the dimension (thickness) of the main body 80 in the longitudinal direction A. A distal surface or a proximal surface of the constricting member 8B is adhered to the accommodating section 16, and an outer circumferential portion of the main body 80 comes into contact with the inner circumferential surface of the accommodating section 16 and is attached thereto. In this example shown, a distal surface of the main body 80 is adhered to a surface of the accommodating section 16 on the distal side.

The hollow pipe 2 is inserted through the through-hole 12 of the pipe holder 11B. The tube main body 20 of the hollow pipe 2 is inserted through the through-hole 12 and the opening 88 of the constricting member 8B. A distance between the base parts 871 of the pair of constricting parts 81B and a distance between the holding base parts 891 of the pair of holding parts 89 are greater than the outer diameter of the hollow pipe 2. The hollow pipe 2 advances and retracts in the opening 88 of the constricting member 8B while coming into contact with the constricting piece 872 and the holding piece 892. The holding piece 892 normally comes into contact with the outer circumferential surface of the hollow pipe 2 while being elastically deformed. The pair of constricting pieces 872 are disposed at positions corresponding to the pair of side holes 27B of the hollow pipe 2, respectively. The constricting piece 872 electrically deforms when it comes into contact with the outer circumferential surface of the hollow pipe 2, and bends with respect to the base part 871 in the longitudinal direction A. When the constricting piece 872 moves to the position of the side hole 27B in accordance with advancement and retraction of the hollow pipe 2, the constricting piece 872 enters the side hole 27B and protrudes into the flow channel 23. In this example, when the hollow pipe 2 is at an accommodating position shown in FIG. 14, the constricting piece 872 comes into contact with the outer circumferential surface of the hollow pipe 2 and elastically deformed on the proximal side to be bent. While not shown, the holding piece 892 also elastically deformed to be bent. When the operation wire 4 and the hollow pipe 2 advance and the constricting piece 872 enters the side hole 27B as shown in FIG. 15, the constricting piece 872 returns to its original shape, extends in the radial direction and protrudes into the flow channel 23. While not shown, the holding piece 892 comes into contact with the outer circumferential surface of the hollow pipe 2 and elastically deformed to be bent. When the operation wire 4 and the hollow pipe 2 retract from a position where the flange 21 of the hollow pipe 2 protrudes to the distal side of the pipe holder 11B, the constricting piece 872 is guided to the outer side of the hollow pipe 2 along the inclined surface of the distal edge 272 of the side hole 27B. In addition, by rotating the hollow pipe 2 around the center axis O, the high water pressure state and the low water pressure state may be switched by varying a relative position between the side hole 27 of the hollow pipe 2 and the constricting piece 872. That is, when the constricting piece 872 is disposed at a position facing the side hole 27, the constricting piece 872 enters the side hole 27B and protrudes into the flow channel 23 to become a high water pressure state. When the operation part is rotated to relatively move the hollow pipe 2 with respect to the sheath 1 around the center axis O, the position of the side hole 27 is deviated from the constricting piece 872, and the constricting piece 872 is removed from the side hole 27, resulting in a low water pressure state.

According to the embodiment, the proximal surface of the constricting piece 872 functions as the constricting surface 811 in accordance with advancement and retraction of the operation wire 4 and the hollow pipe 2. The constricting piece 872 smoothly protrudes in the flow channel 23 in accordance with advancement and retraction of the operation wire 4 and the hollow pipe 2 with respect to the sheath 1, and the opening area of the flow channel 23 can be more reliably narrowed. Meanwhile, the constricting piece 872 returns to the original position where it does not protrude in the flow channel 23 in accordance with the operation of retracting the operation wire 4 and the hollow pipe 2. As a result, switching of the water force of the liquid supplied from the distal opening 22*a* via the flow channel 23 is reliably performed. Accordingly, the treatment tool 100 is configured to change between the low water pressure configuration and high water pressure configuration to easily change the water force of the liquid supplied from the distal opening 22*a* in accordance with relative movement of the hollow pipe 2 with respect to the sheath 1.

In this example, while the example in which the constricting member 8B has the pair of constricting parts 81B and the pair of holding parts 89 has been described, the constricting member is not limited thereto. For example, the constricting part 81B may be provided by one or three or more. The holding part 89 has a function of stably holding the hollow pipe 2 upon advance and retract of the hollow pipe 2. The holding part 89 is not an essential configuration of the constricting member 8B for the purpose of changing the water force of the flow channel 23.

According to the treatment tool 100B of the embodiment, a plurality of treatments such as local injection treatment, incision peeling treatment, hemostasis treatment, additional local injection, operation site cleaning, and the like, can be performed using the same using method as that of the treatment tool 100 of the first embodiment. According to the treatment tool 100 of the embodiment, a plurality of treatments such as local injection treatment, incision peeling treatment, hemostasis treatment, additional local injection, operation site cleaning, and the like, can be performed without insertion and removal of the treatment tool 100 into/from the channel 206 of the endoscope 200.

Hereinabove, while the second embodiment of the present disclosure has been described in detail with reference to the accompanying drawings, a specific configuration is not limited to the embodiment and also includes design changes or the like without departing from the spirit of the present disclosure. In addition, the components shown in the above-mentioned embodiment and modified examples may be combined appropriately.

While the example in which the distal edge 272 of the side hole 27B is inclined has been described in the embodiment, the shape of the side hole 27B is not limited thereto. The side hole 27B may be open such that the constricting piece 872 of the constricting part 81B protrudes or retracts.

Modified Example 2-1

Figure 17:
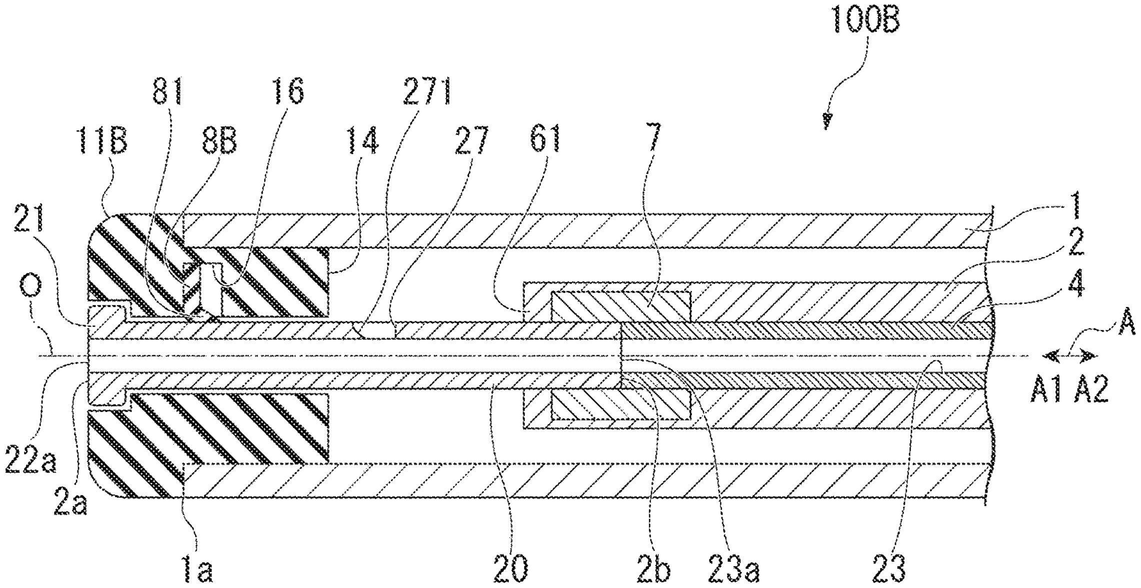
FIG. 17 is a cross-sectional view of a distal end portion of a treatment tool of a modified example of the second embodiment.
Figure 18:
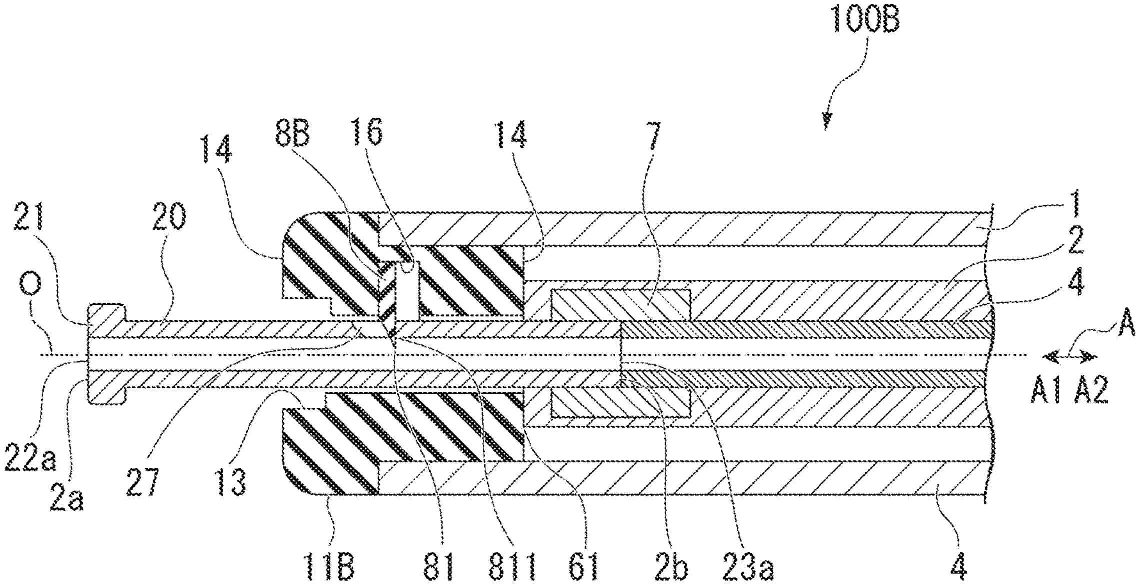
FIG. 18 is a cross-sectional view of a distal end portion of a treatment tool of a modified example of the second embodiment.

A modified example of the embodiment will be described with reference to FIG. 17 and FIG. 18. As shown in FIG. 17 and FIG. 18, the constricting member 8B may be disposed in a part of the hollow pipe 2 in the circumferential direction. The constricting member 8B of the example has a semi-circular shape when seen in the longitudinal direction A. For example, the constricting member 8B may be disposed in a part of the hollow pipe 2 in the circumferential direction, for example, a semi-circular shape, a fan shape, a three-fourths arc, or the like, when seen in the longitudinal direction A. In this example, one constricting part 81B is provided. An operation of the constricting piece 872 in accordance with advancement and retraction of the hollow pipe 2 is the same as in the second embodiment. The accommodating section 16 of the pipe holder 11B is formed in a part of the through-hole 12 in the circumferential direction to correspond to the shape of the constricting part 81B. According to the treatment tool 100B of the example, like the second embodiment, the constricting piece 872 elastically deforms in accordance with advancement and retraction of the hollow pipe 2, and is capable of protruding and retracting in the flow channel 23 from the side hole 27B. Accordingly, the opening area of the flow channel 23 is configured to be more reliably narrowed by the constricting piece 872, and switching of the water force of the flow channel 23 by the constricting part 81 is reliably performed. Accordingly, the treatment tool 100 is configured to be easily change the water force of the liquid supplied from the distal opening 22*a*. Like the modified example, a contact area between the constricting piece 872 and the outer surface of the hollow pipe 2 is kept small and the hollow pipe 2 is capable of advancing and retracting smoothly due to the configuration of providing the constricting member 8B in the part of the hollow pipe 2 in the circumferential direction.

According to the treatment tool 100B of the embodiment and modified example, the constricting part 81B is configured to protrude from or retract into the flow channel 23 and the opening area of the flow channel 23 is capable of being changed in accordance with the operation of causing the operation wire 4 and the hollow pipe 2 to advance and retract with respect to the sheath 1. That is, the opening area of the flow channel 23 can be changed and the water force of the liquid supplied from the distal opening 22*a* via the flow channel 23 can be changed by advancing and retracting the slider 52 of the operation part 5. Accordingly, for example, the liquid can be supplied from the distal opening 22*a* in a state in which the water force is high during local injection and re-local injection, and the liquid can be supplied from the distal opening 22*a* in a state in which the water force is low during operation site cleaning.

Modified Example 2-2

Figure 19:
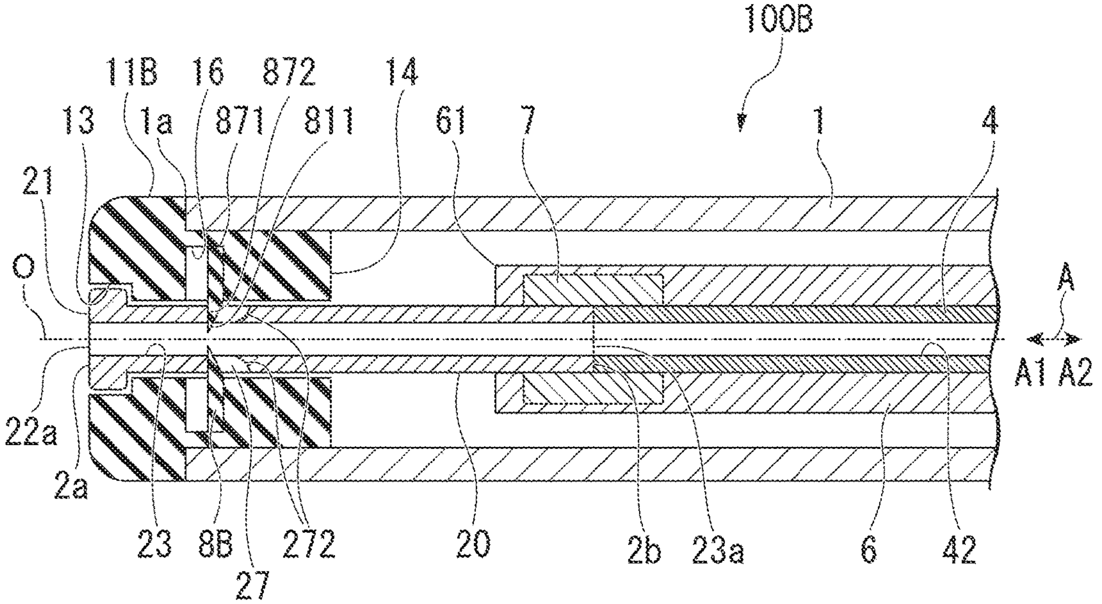
FIG. 19 is a cross-sectional view of a distal end portion of a treatment tool of a modified example of the second embodiment.
Figure 20:
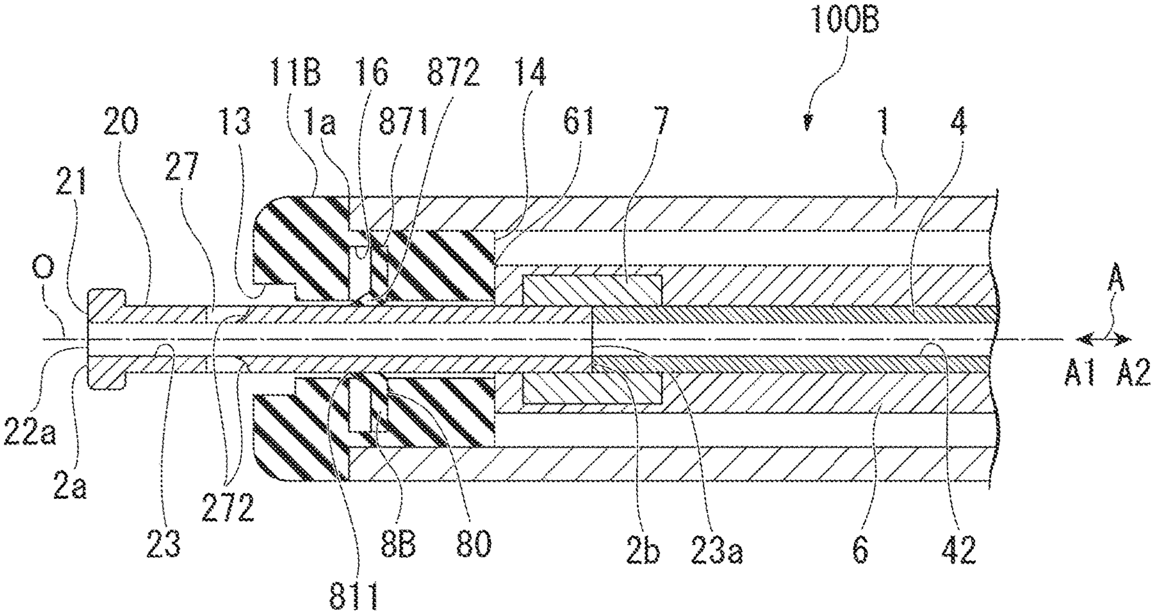
FIG. 20 is a cross-sectional view of a distal end portion of a treatment tool of a modified example of the second embodiment.

A modified example of the embodiment will be described with reference to FIG. 19 and FIG. 20. As shown in FIG. 19 and FIG. 20, the side hole 27B may be located on the distal side A1 further than in the embodiment. The side hole 27B of the example is located on the distal side A1 by a half between the distal end 2*a* of the hollow pipe 2 and the distal end 61 of the cover tube 6 when the hollow pipe 2 is seen in a direction crossing the center axis O. More specifically, the side hole 27B is disposed at a position where the constricting member 8B intrudes into the side hole 27B in a state in which the flange 21 is accommodated in the stepped portion 13.

According to the above-mentioned configuration, the base part 871 of the constricting part 81 can protrude from the side hole 27B in the radial direction to narrow the flow channel 23 when the flange 21 is accommodated in the stepped portion 13, resulting in the state in which the water pressure is high. At this time, the distal edge 272 of the side hole 27B is inclined from the proximal end of the center axis O toward the distal end.

Third Embodiment

A treatment tool 100C according to a third embodiment of the present disclosure will be described with reference to FIG. 21 to FIG. 23. In the following description, the common components as those as already described are designated by the same reference signs and overlapping description will be omitted.

Figure 21:
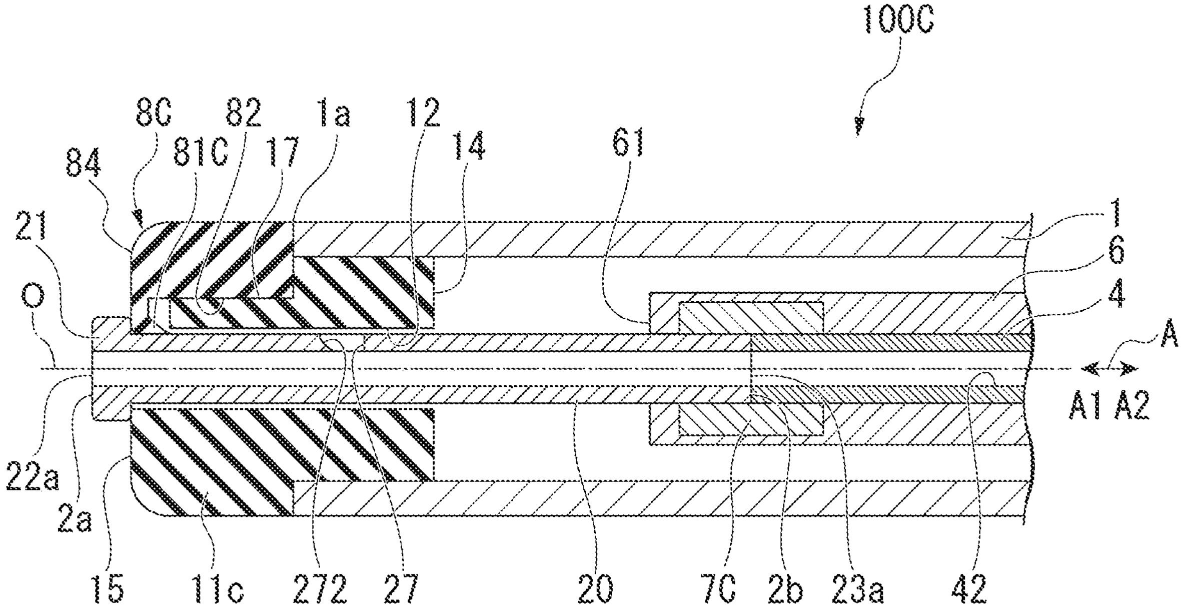
FIG. 21 is a cross-sectional view of a distal end portion of a treatment tool of a third embodiment.
Figure 22:
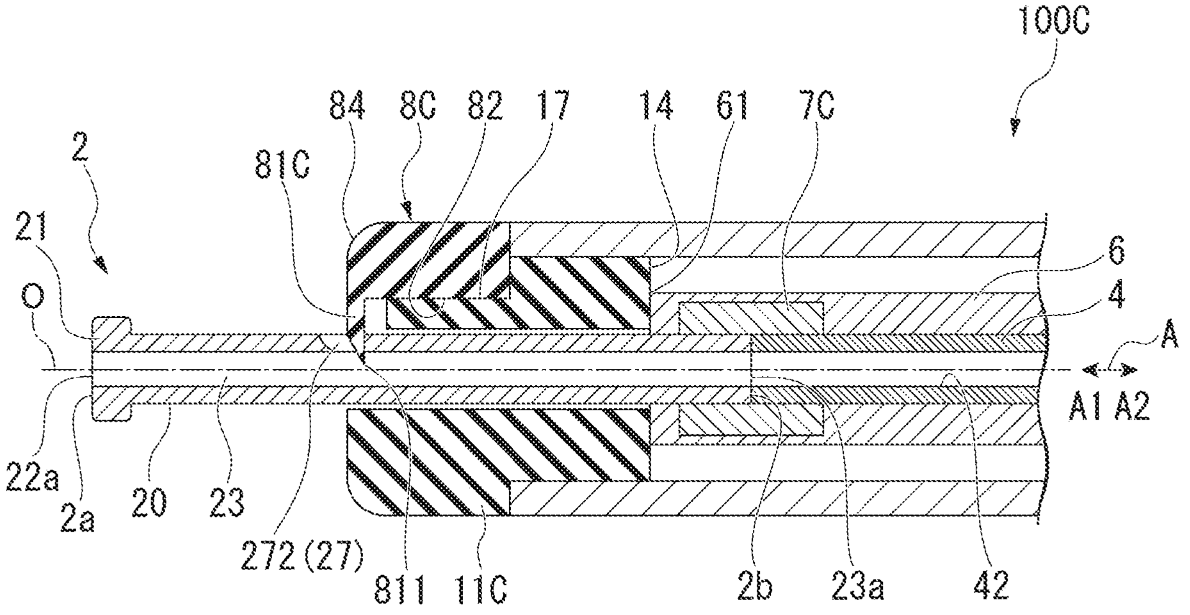
FIG. 22 is a cross-sectional view of the distal end portion of the treatment tool of the third embodiment.
Figure 23:
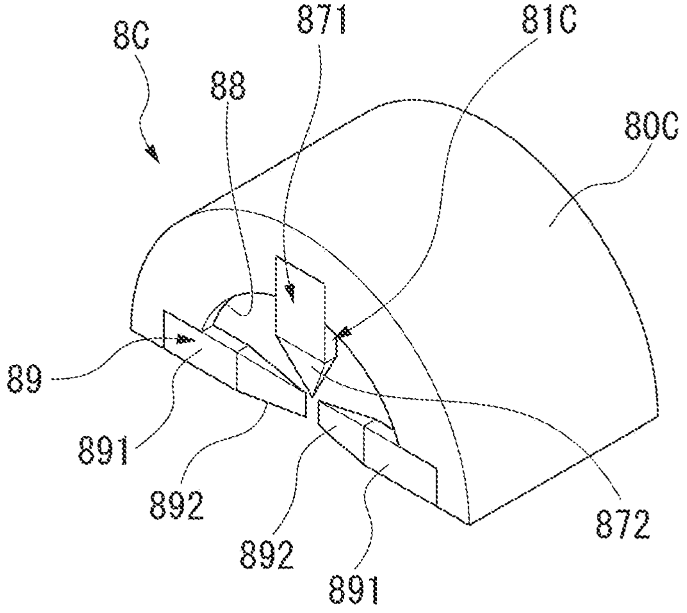
FIG. 23 is a perspective view of a constricting member of the third embodiment.

FIG. 21 and FIG. 23 are cross-sectional view showing a distal end portion of the treatment tool 100C. Like the treatment tool 100 of the first embodiment, the treatment tool (treatment tool for an endoscope) 100C constitutes an endoscope treatment system together with the endoscope 200. The treatment tool 100C includes a sheath 1C, a hollow pipe 2, a pipe holder 11C, a constricting member 8C, an operation wire 4, a connecting pipe 7C, and an operation part 5. The connecting pipe 7C, the operation wire 4, and the hollow pipe 2 have the same configurations as in the second embodiment.

In the embodiment, the constricting member 8C is attached to the pipe holder 11C. The constricting member 8C is attached to the distal end 1*a* of the sheath 1 on the distal side A1. Specifically, the constricting member 8C is provided on a portion of the pipe holder 11C protruding from the distal end 1*a* of the sheath 1. FIG. 23 is a perspective view of the constricting member 8C. The constricting member 8C is a resin member having insulation. The constricting member 8C has a main body 80C, a constricting part 81C, and a holding part 89. The main body 80C has an arc shape with a size that is flush with the outer circumferential surface of the sheath 1. The main body 80C has a contacting surface 82C to the pipe holder 11C. As shown in FIG. 21 and FIG. 22, a portion of the pipe holder 11C protruding from the distal end 1*a* of the sheath 1 on the distal side has a distal stepped portion 17 having a thickness in the radial direction that is smaller than the proximal end portion inserted and fixed into the distal end portion of the sheath 1. The inner circumferential surface of the main body 80C constitutes the contacting surface 82. The contacting surface 82C is disposed to face the outer circumferential surface of the distal stepped portion 17 of the pipe holder 11C, and contacts and fixed to the distal stepped portion 17. An opening 88 is formed in a distal part of the main body 80C on the side of the center axis O of the sheath 1 and the pipe holder 11C.

The constricting part 81C is a protrusion extending from the main body 80C toward the center axis O of the pipe holder 11C in the radial direction. The constricting part 81C protrudes toward the through-hole 12 from the contacting surface 82. The constricting part 81C has a base part 871 and a constricting piece 872 from the opening 88 in the radial direction. The base part 871 is a columnar part extending from the opening 88 in the radial direction. The constricting piece 872 has a square pyramid shape tapered from the base part 871 toward the center axis O of the pipe holder 11C. The constricting piece 872 is configured to be softer than the base part 871 and elastically deformable when an external force is applied. The pair of holding parts 89 are provided to protrude from positions separated 180 degrees in the circumferential direction of the main body 80C. The constricting part 81C is provided between the pair of holding parts 89.

When the constricting member 8C is fixed to the distal stepped portion 17 of the pipe holder 11C, in a natural state in which an external force is not applied to the constricting part 81C, the constricting part 81C protrudes toward the center axis O from the inner circumferential surface of the through-hole 12. The constricting part 81C protrudes to a position where it comes into contact with the outer surface of the hollow pipe 2 inserted through the through-hole 12. The constricting piece 872 is disposed at a position corresponding to the side hole 27 of the hollow pipe 2. The constricting piece 872 elastically deforms when it comes into contact with the outer circumferential surface of the hollow pipe 2, and bends with respect to the base part 871 in the longitudinal direction A. When positions of the constricting piece 872 and the side hole 27 in the longitudinal direction A coincide with each other in accordance with advancement and retraction of the hollow pipe 2, the constricting piece 872 enters the side hole 27 and protrudes inside the flow channel 23. In this example, as shown in FIG. 21, when the hollow pipe 2 is located at a retracted position, the constricting piece 872 comes into contact with the outer circumferential surface of the hollow pipe 2 and elastically deformed to be bent on the proximal side. While not shown, the holding piece 892 also elastically deforms and bends. When the operation wire 4 and the hollow pipe 2 advance and the constricting piece 872 enters the side hole 27 as shown in FIG. 22, the constricting piece 872 returns to the original shape, extends in the radial direction and protrudes in the flow channel 23. While not shown, the holding piece 892 comes into contact with the outer circumferential surface of the hollow pipe 2 and elastically deforms to be bent. As shown in FIG. 21, the constricting part 81C is elastically deformed by a load of an external force, and a low water pressure configuration without interfering with the flow channel 23 is configured. As shown in FIG. 22, in a natural state in which an external force is not applied, the constricting part 81 returns to the original shape to configure the high water pressure configuration from the low water pressure configuration. Accordingly, the treatment tool 100C is configured to change between the low water pressure configuration and the high water pressure configuration in accordance with relative movement of the hollow pipe 2 with respect to the sheath 1, and is configured to be easily change the water force of the liquid supplied from the distal opening 22*a*.

According to the treatment tool 100C of the embodiment, like the first embodiment, a plurality of treatments such as local injection treatment, incision peeling treatment, hemostasis treatment, additional local injection, operation site cleaning, and the like, can be performed. According to the treatment tool 100 of the embodiment, a plurality of treatments such as local injection treatment, incision peeling treatment, hemostasis treatment, additional local injection, operation site cleaning, and the like, can be performed without insertion and removal of the treatment tool 100 into/from the channel 206 of the endoscope 200.

According to the treatment tool 100C of the embodiment, since the constricting member 8C is disposed at a position protruding from the distal end 1*a* of the sheath 1, the constricting part 81C can be disposed at a position where the constricting part 81C is closest to the projection end of the hollow pipe 2. As a result, the water force can be increased by the constricting part 81C at a position closer to the distal opening 22*a* of the hollow pipe 2. Accordingly, since a distance between the position where the liquid in the flow channel 23 is at a high water pressure and the distal opening 22*a* is short, the water force discharged from the distal opening 22*a* can be increased.

Hereinabove, while the third embodiment of the present disclosure has been described in detail with reference to the accompanying drawings, a specific configuration is not limited to the embodiment and also includes design changes or the like without departing from the spirit of the present disclosure. In addition, the components shown in the above-mentioned embodiment and modified examples may be combined appropriately. In the following description, the common components as those as already described are designated by the same reference signs and overlapping description will be omitted.

Modified Example 3-1

Figure 24:
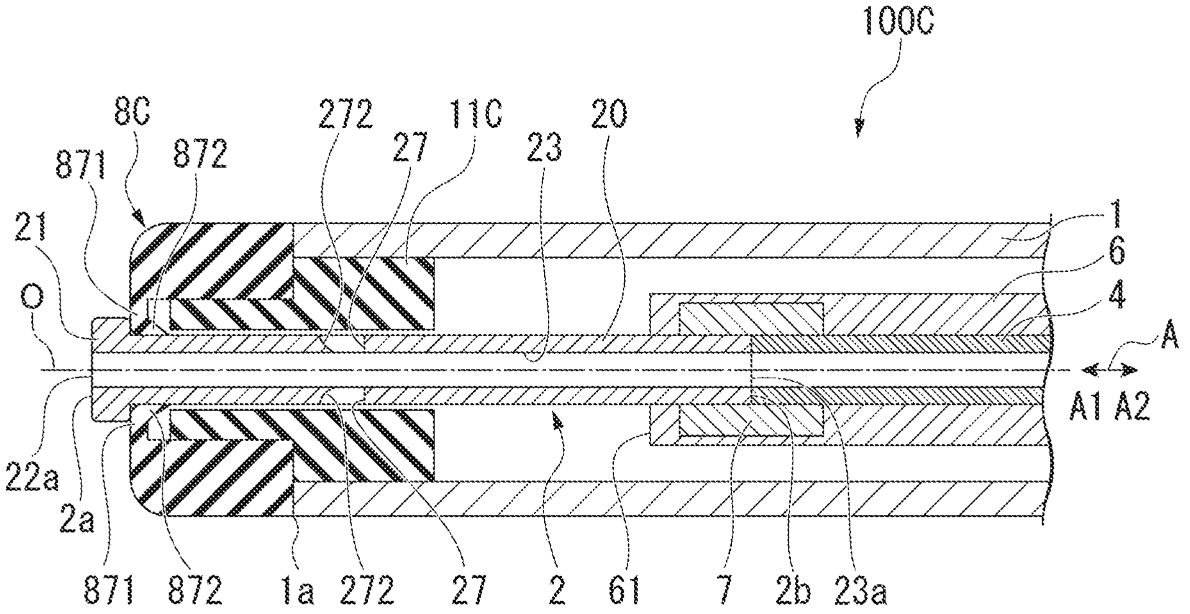
FIG. 24 is a cross-sectional view of a distal end portion of a treatment tool of a modified example of the third embodiment.
Figure 25:
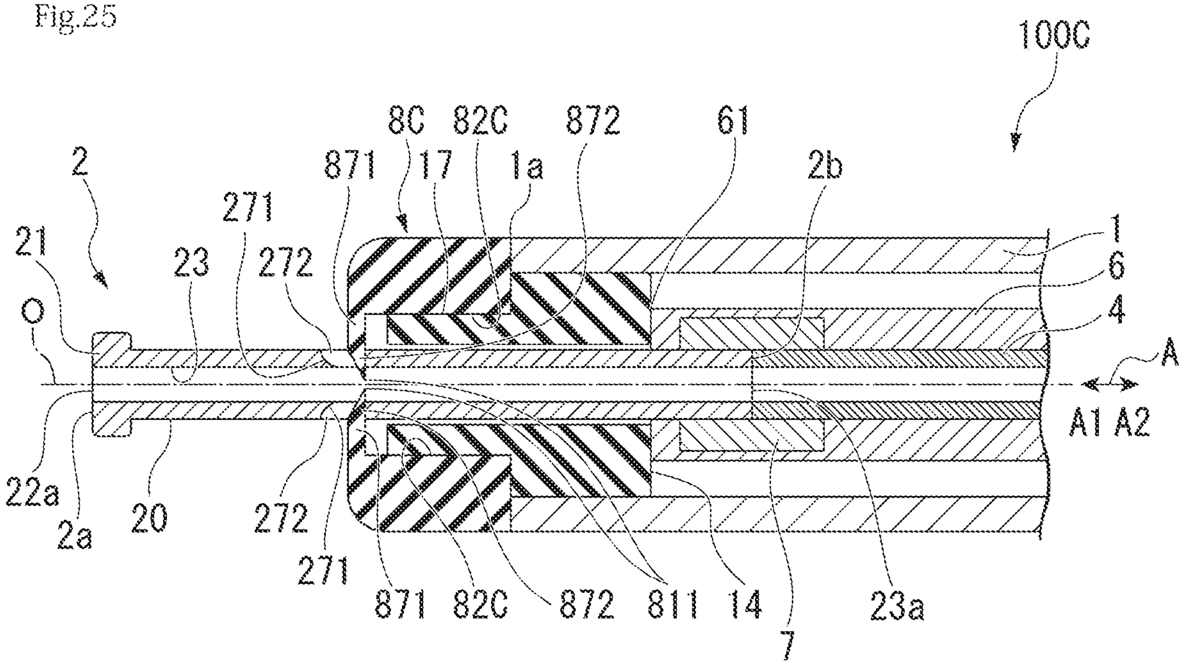
FIG. 25 is a cross-sectional view of a distal end portion of a treatment tool of a modified example of the third embodiment.
Figure 26:
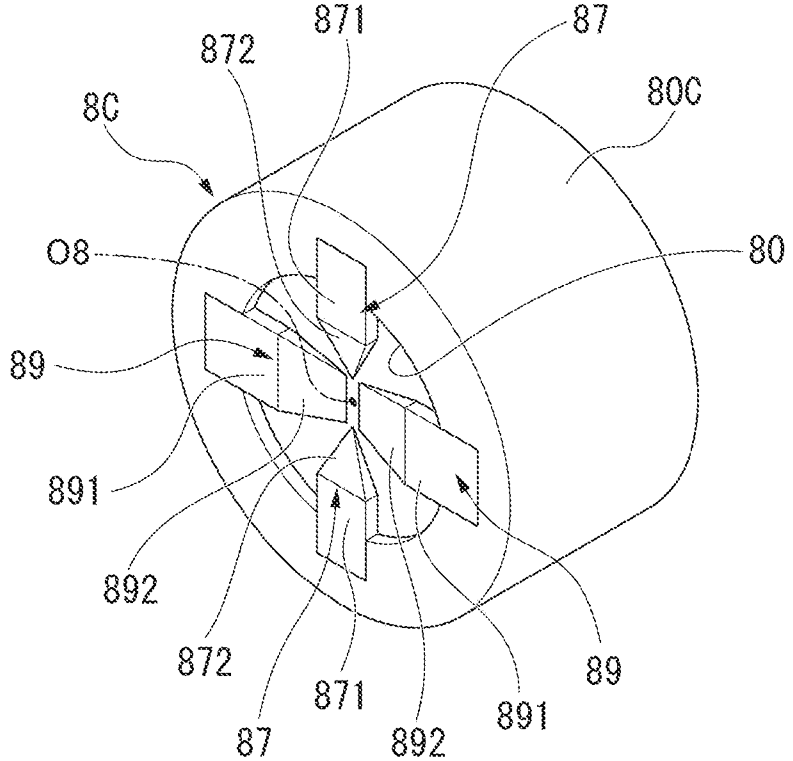
FIG. 26 is a perspective view of a constricting member of a modified example of the third embodiment.

A modified example of the embodiment will be described with reference to FIG. 24 to FIG. 26. The constricting member may include a constricting part that is changeable between a position disposed in the flow channel 23 of the hollow pipe 2 and blocking a part of the flow channel and a position without interfering with the flow channel 23, and it is not limited to the example shown in FIG. 23. In addition, the number of the constricting part 81 and the side hole 27 is not limited to one and may be plural. As shown in FIG. 24 and FIG. 25, the constricting member 8C may be provided at a position that covers the entire circumference of the distal end of the pipe holder 11C. The constricting member 8C of the example has a circular shape when seen in the longitudinal direction A. In this example, the pair of side holes 27 are open at facing positions with the center axis O of the hollow pipe 2 sandwiched therebetween, and the constricting part 81C includes the pair of constricting parts 81 at positions corresponding to the pair of side holes 27. The pair of holding parts 89 are provided between the pair of constricting parts 81B in the circumferential direction. The flange 21 of the hollow pipe 2 is disposed on the distal side of the constricting member 8C. The distal part of the pipe holder 11C has a diameter smaller than that of the insertion part into the distal end 1*a* of the sheath 1. The constricting member 8C is attached to cover the outer circumference of the distal part of the pipe holder 11C from the distal side of the pipe holder 11C. The inner circumferential surface of the main body 80C configures the contacting surface 82. The constricting member 8C are mounted and attached to the distal part of the pipe holder 11C from the outside. An operation of the constricting piece 872 in accordance with advancement and retraction of the hollow pipe 2 is the same as in the third embodiment.

According to the configuration in which the pair of constricting parts 81C protrude and retract into the flow channel 23 from the outside of the pair of side holes 27, a difference between a place where the opening area of the flow channel 23 is wide and a place where it is narrow can be increased, and the liquid can be supplied in a state in which the water force is higher. Meanwhile, when the operation wire 4 and the hollow pipe 2 retract, the pair of constricting parts 81C are moved to the outer side of the hollow pipe 2 and changed to a state in which the constricting part 81 does not interfere with the flow channel 23. Accordingly, the water force of the liquid supplied from the distal opening 22*a* can be largely changed.

Figure 10:
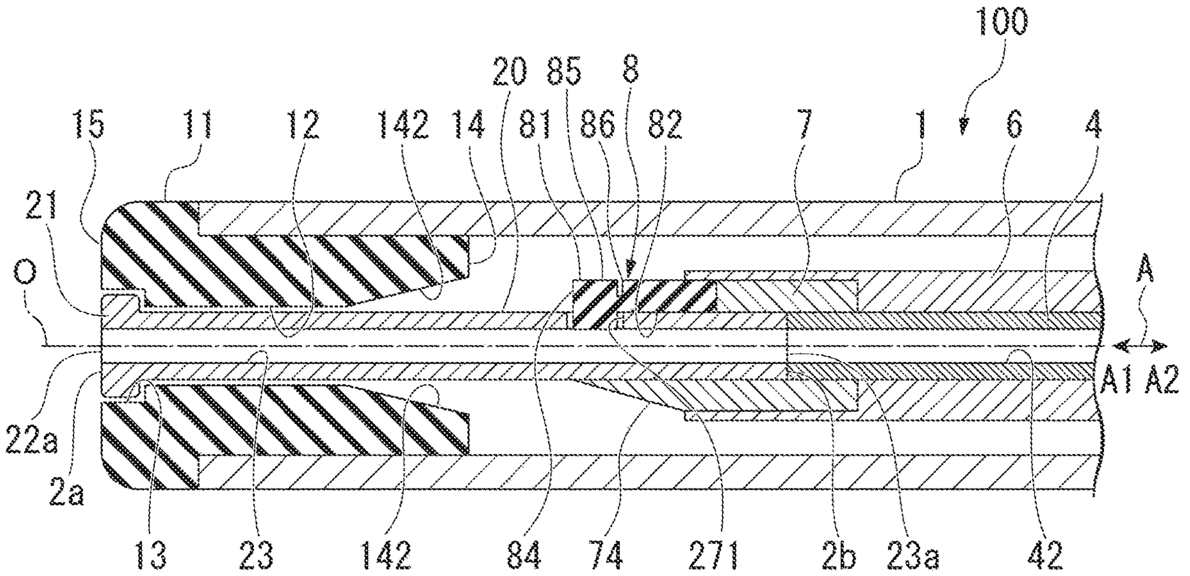
FIG. 10 is a cross-sectional view of a distal end portion of a treatment tool of a modified example of the first embodiment.
Figure 11:
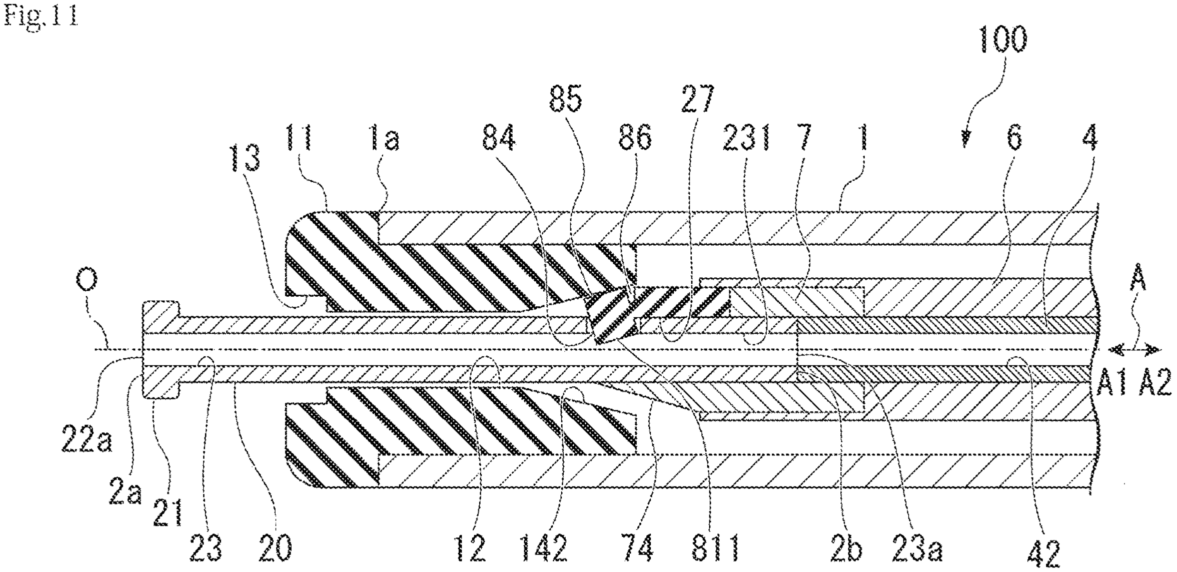
FIG. 11 is a cross-sectional view of a distal end portion of a treatment tool of a modified example of the first embodiment.

While not shown, the slit 86 shown in FIG. 10 and FIG. 11 may be provided in each of the constricting parts in the example. The holding part 89 has a function of stably holding the hollow pipe 2 upon advance and retract of the hollow pipe 2. The holding part 89 is not an essential configuration of the constricting member 8B for the purpose of changing the water force of the flow channel 23.

Fourth Embodiment

Figure 28:
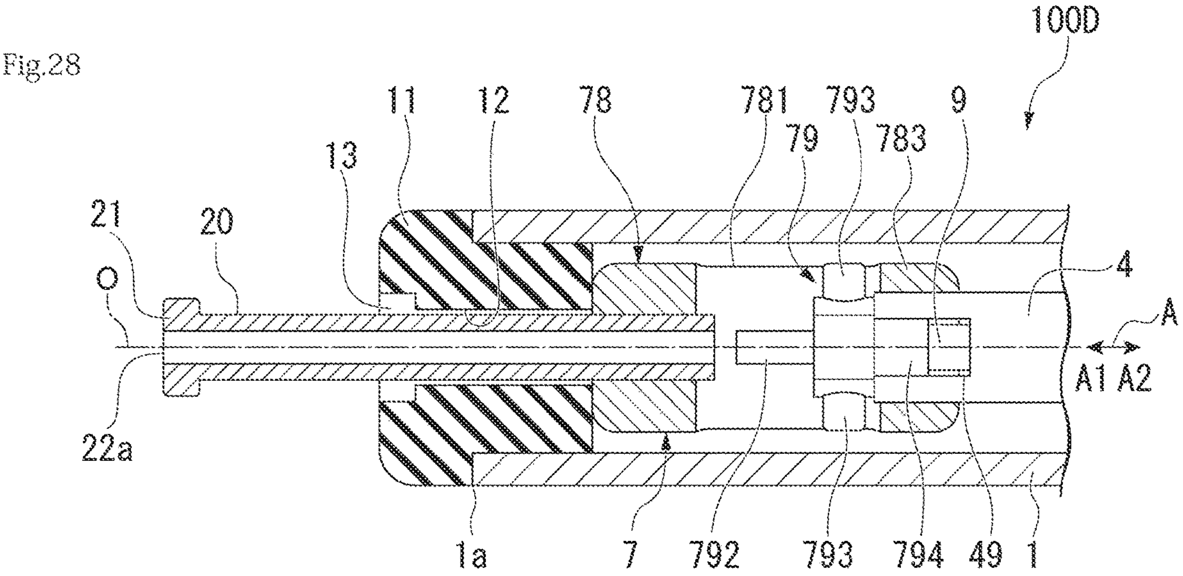
FIG. 28 is a cross-sectional view of the distal end portion of the treatment tool of the fourth embodiment.
Figure 29:
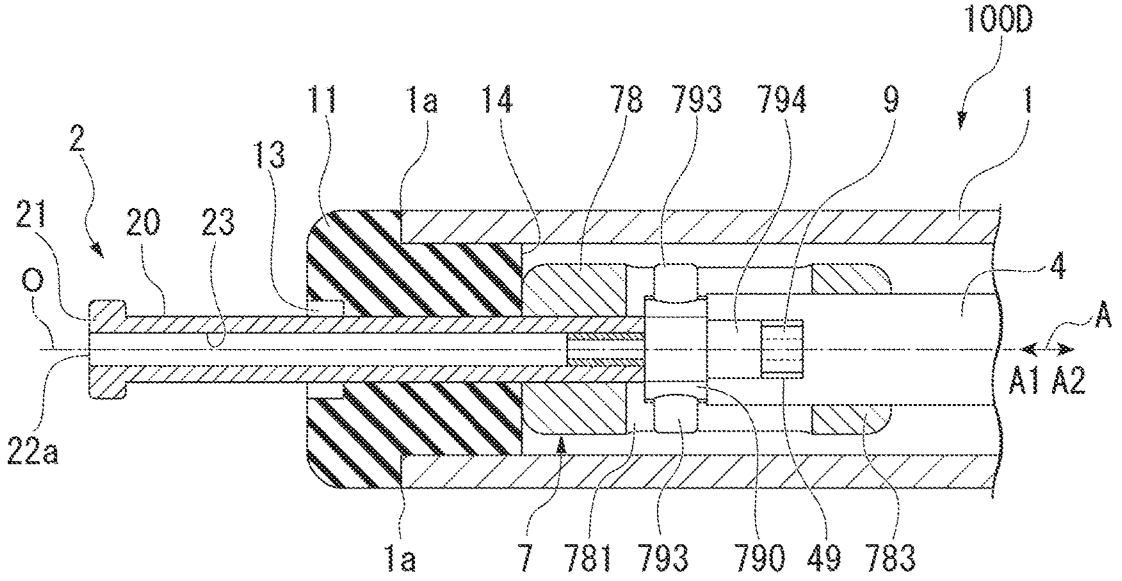
FIG. 29 is a cross-sectional view of the distal end portion of the treatment tool of the fourth embodiment.

A treatment tool 100D according to a fourth embodiment will be described with reference to FIG. 27 to FIG. 29. In the following description, the same components as described already are designated by the same reference signs and overlapping descriptions thereof will be omitted.

Figure 27:
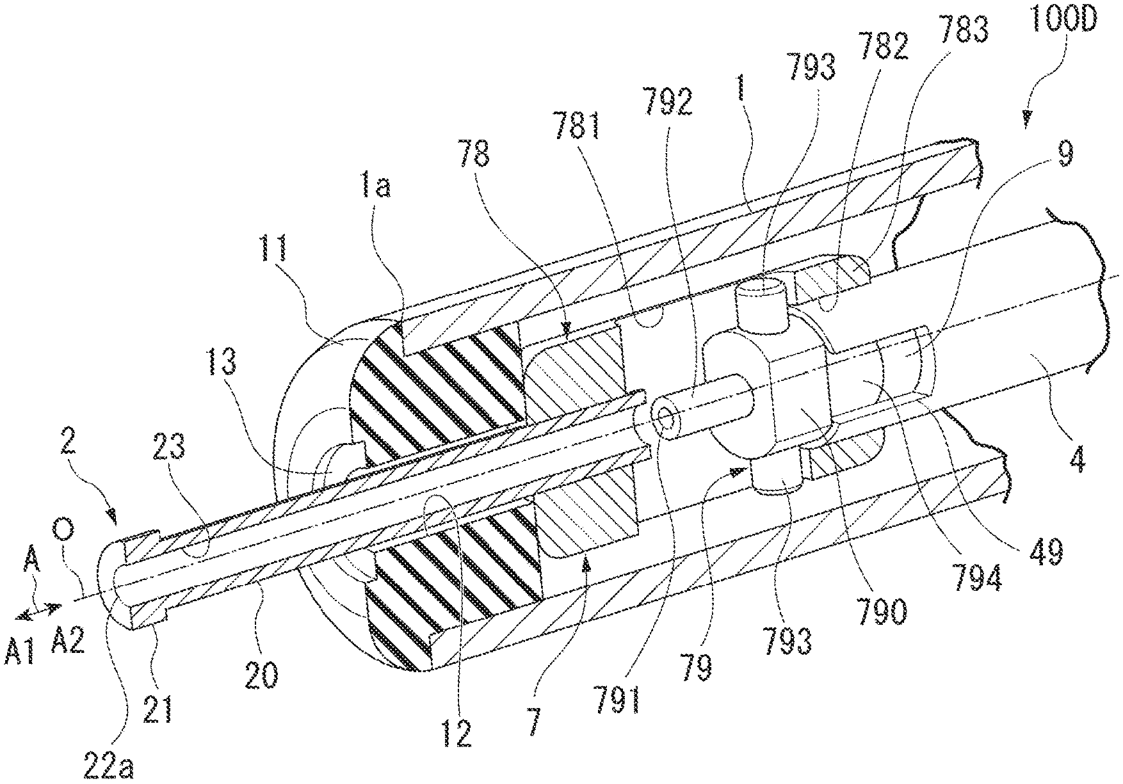
FIG. 27 is a cross-sectional perspective view of a distal end portion of a treatment tool of a fourth embodiment.

FIG. 27 is a perspective view showing a distal part of the treatment tool 100D according to the fourth embodiment, a part of which is shown in a cross section in the longitudinal direction A. The treatment tool 100D includes a sheath 1, a hollow pipe 2, a pipe holder 11, a connecting member 7, an operation wire 9 for flow channel adjustment, an operation wire 4 for a knife, and an operation part 5. The sheath 1, the pipe holder 11, and the operation wire 4 for a knife are the same as in the above-mentioned embodiment. The hollow pipe 2 does not include the side hole 27 of the above-mentioned embodiment. The other configurations are the same as in the above-mentioned embodiment. The operation wire 9 for flow channel adjustment is a wire having a hollow portion configured to advance and retract the hollow pipe 2 with respect to the sheath 1. The operation wire 9 for flow channel adjustment is hollow inside the entire length. The operation wire 9 for flow channel adjustment is inserted into the operation wire 4 for a knife.

The connecting member 7 is a member configured to connect the hollow pipe 2 and the operation wire 4 for a knife. The connecting member 7 has a main body 78 and a flow channel adjustment member 79. The main body 78 has a through-hole formed along the center axis O, and a slit 781. The slit 781 is a space formed in a central portion of the connecting member 7 in the longitudinal direction A. A proximal end portion of the hollow pipe 2 is inserted and fixed to the through-hole on the distal side of the slit 781. According to the configuration, the connecting member 7 also advances and retracts in accordance with advancement and retraction of the slider 52, and as a result, the hollow pipe 2 connected to the connecting member 7 advances and retracts. An opening of the proximal end of the hollow pipe 2 is opened in the slit 781. The operation wire 9 is inserted and fixed to the through-hole on the proximal side of the slit 781. A water discharge port 49 obtained by opening a part of a sidewall in the circumferential direction is formed in the distal end portion of the operation wire 4 for a knife.

The flow channel adjustment member 79 has a base part 790, a first pipe 792, a second pipe 794, and a guide protrusion 793. The first pipe 792 is a pipe located on the distal side of the base part 790. The second pipe 794 is a pipe located on the proximal side of the base part 790. The base part 790 has a guide surface disposed in parallel to the inner wall of the slit 781, and a through-hole passing along the center axis O. The guide protrusion 793 protrudes in a direction substantially perpendicular to the center axis O. In this example, the pair of guide protrusions 793 are provided, and each of the guide protrusion 793 protrudes from a base part 793 in a direction different from a direction substantially perpendicular to the center axis O.

The first pipe 792, the base part 790, and the second pipe 794 are in communication with each other along the center axis O. The second pipe 794 is fixed to a distal end of the operation wire 9 for flow channel adjustment. The liquid supplied to the operation wire 9 for flow channel adjustment like the embodiment passes through the second pipe 794, the base part 790, and the first pipe 792, and the liquid can be discharged from a distal opening 791 of the first pipe 792. Further, the liquid can also be supplied into the lumen of the operation wire 4 for a knife, and the liquid passing through a space between the lumen of the operation wire 4 for a knife and the operation wire 9 for flow channel adjustment is discharged from the water discharge port 49 of the operation wire 4 for a knife.

The flow channel adjustment member 79 is disposed in the slit 781. The flow channel adjustment member 79 is slidable in the slit 781 along the center axis O.

Figure 30:
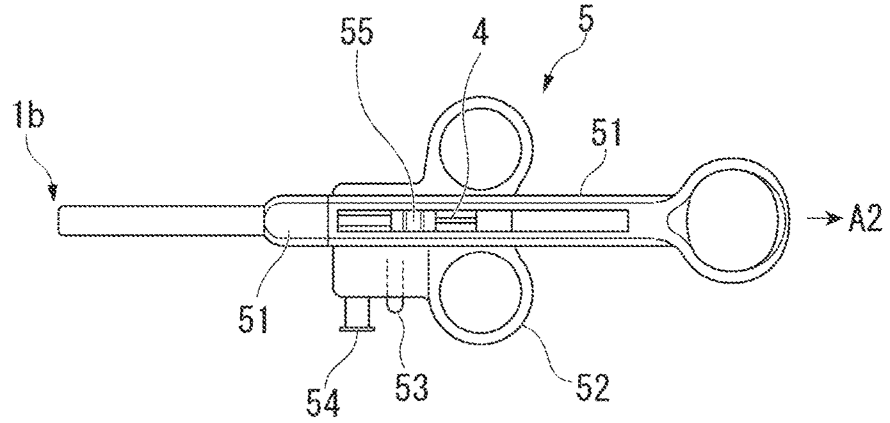
FIG. 30 is a side view of an operation part of the treatment tool of the fourth embodiment.

As shown in FIG. 30, the operation part 5C according to the embodiment has a lever 55. The operation wire 4 for a knife can advance and retract in accordance with the operation of the slider 52 of the operation part independently from the operation wire 9 for flow channel adjustment. The connecting member 7 advances and retracts in accordance with an advancing and retracting operation of the operation wire 4 for a knife. Since the hollow pipe 2 is fixed to the connecting member 7, the hollow pipe 2 advances and retracts with respect to the sheath 1 in accordance with the operation of the operation wire 4 for a knife. The operation wire 9 for flow channel adjustment and the flow channel adjustment member 79 are provided to advance and retract with respect to the sheath 1 in accordance with the advance and retract operation of the lever 55. The operation wire 9 for flow channel adjustment is able to advance and retract with respect to the operation wire 4 for a knife. The flow channel adjustment member 79 advances and retracts in the slit 781 of the connecting member 7 in accordance with advancement and retraction of the operation wire 9 for flow channel adjustment. At a position where the flow channel adjustment member 79 comes into contact with the proximal end in the slit 781, the distal opening 791 of the first pipe 792 is separated from the proximal end of the hollow pipe 2 to the proximal side and is opened in the slit 781. As shown in FIG. 29, at a position where the flow channel adjustment member 79 advances to the distal side in the slit 781, the distal opening 791 of the first pipe 792 enters the flow channel 23 from the proximal end of the hollow pipe 2 and comes into contact with the flow channel 23.

When the liquid is supplied into the operation wire 9 for flow channel adjustment at a position where the distal opening 791 of the first pipe 792 and the proximal end of the hollow pipe 2 are separated, the liquid flows into the proximal end of the hollow pipe 2, and the liquid is supplied from the distal opening 22*a* of the hollow pipe 2. When the liquid is supplied into the operation wire 9 for flow channel adjustment at the position where the distal opening 791 of the first pipe 792 and the proximal end of the hollow pipe 2 are separated, the liquid flowing in the flow channel of the hollow pipe 2 flows in the low water pressure configuration. When the liquid is supplied in a state in which the flow channel adjustment member 79 advances and the distal opening 791 of the first pipe 792 is connected to the flow channel 23 of the hollow pipe 2, the liquid passes through the first pipe 792 having an opening area smaller than that of the flow channel 23, the water pressure is increased, and it becomes the high water pressure configuration. When the liquid flows in the high water pressure configuration, the water force of the liquid supplied from the distal opening 22*a* of the hollow pipe 2 is increased.

According to the treatment tool 100D of the embodiment, a plurality of treatments can be performed. According to the treatment tool 100D of the embodiment, a plurality of treatment such as local injection treatment, incision peeling treatment, hemostasis treatment, additional local injection, operation site cleaning, and the like, can be performed without insertion and removal of the treatment tool 100D from/into the channel 206 of the endoscope 200.

According to the treatment tool 100D of the embodiment, a place where the opening area is small can be provided in the flow channel 23 and the water force of the liquid can be increased by inserting the flow channel adjustment member 79 into the flow channel 23 of the hollow pipe 2. That is, it is possible to change between the high water pressure configuration and the low water pressure configuration in accordance with a slide operation of the operation part.

According to the treatment tool 100D of the embodiment, regardless of a protrusion state of the hollow pipe 2 with respect to the sheath 1, it is possible to change between the high water pressure configuration and the low water pressure configuration.

Hereinabove, while the fourth embodiment has been described in detail with reference to the accompanying drawings, the specific configuration is not limited to the embodiment, and also includes design changes or the like without departing from the spirit of the present disclosure. In addition, the components shown in the above-mentioned embodiment and modified examples may be combined appropriately. While the example in which the liquid can also flow between the lumen of the operation wire 4 for a knife and the operation wire 9 for flow channel adjustment has been described in the embodiment, the configuration in which the liquid can also flow between the lumen of the operation wire 4 for a knife and the operation wire 9 for flow channel adjustment is not an essential configuration for the purpose of changing the water force of the liquid supplied from the distal opening 22*a* of the hollow pipe 2.

The treatment tool 100 according to each of the embodiments includes the stepped portion 13, and thus, upon retract of the hollow pipe 2, the flange 21 can be accommodated in the stepped portion 13. While the example in which the stepped portion 13 is formed in the distal end of the pipe holder 11 has been described in the above-mentioned embodiment, the stepped portion 13 is not an essential configuration for the purpose of adjusting the water force of the liquid supplied.

While some embodiments of the disclosure have been described and illustrated above, it should be understood that these are exemplary of the disclosure and are not to be considered as limiting. Additions, omissions, substitutions, and other modifications can be made without departing from the spirit or scope of the present disclosure. Accordingly, the disclosure is not to be considered as being limited by the foregoing description, and is only limited by the scope of the appended claims.

What is claimed is:

1. A treatment tool, comprising:
- a sheath;
- an electrode located in the sheath, the electrode includes a flow channel formed along a longitudinal axis of the electrode and extending between a distal end and a proximal end of the electrode;
- a holder fixed to a distal end of the sheath and having a through hole in which the electrode is inserted;
- an elastic member located on an outer surface of the electrode; and
- a hollow operation wire connected to the proximal end of the electrode,
- wherein the hollow operation wire includes a second flow channel,
- wherein the second flow channel of the hollow operation wire is in communication with the flow channel of the electrode, and
- wherein a cross-sectional area of the second flow channel of the hollow operation wire is smaller than a cross-sectional area of the flow channel of the electrode.

2. A treatment tool, comprising:
- a sheath;
- an electrode located in the sheath, the electrode includes a flow channel formed along a longitudinal axis of the electrode and extending between a distal end and a proximal end of the electrode;
- a holder fixed to a distal end of the sheath and having a through hole in which the electrode is inserted; and
- an elastic member located on an outer surface of the electrode,
- wherein the elastic member includes a first end that is reversibly inserted into the flow channel,
- wherein the electrode includes a sidewall and an opening formed in the sidewall and in communication with the flow channel,
- wherein the electrode is displaceable relative to the sheath between the electrode first position and an electrode second position, and
- wherein, in the electrode first position, the first end of the elastic member is inserted into the flow channel through the opening and, in the electrode second position, the first end of the elastic member is removed from the flow channel.

3. The treatment tool according to claim 2, wherein, in the electrode first position, a cross-section of the flow channel at a position at which the first end of the elastic member is inserted has a first area,
- wherein, in the electrode second position, the cross-section of the flow channel at the position at which the first end of the elastic member is inserted has a second area, and
- wherein the first area is less than the second area.

4. The treatment tool according to claim 2, wherein the elastic member includes a contacting portion having a contacting surface in contact with the outer surface of the electrode.

5. The treatment tool according to claim 4, wherein, in the second position, the first end of the elastic member is deformed by application of an external force.

6. The treatment tool according to claim 5, wherein, in the electrode first position, the first end of the elastic member is not deformed.

7. The treatment tool according to claim 4, wherein the elastic member includes a slit extending from an outer circumferential surface of the elastic member in a direction perpendicular to the longitudinal axis of the electrode, and
- wherein the slit is located at a proximal portion of the opening formed in the sidewall of the electrode or is located distal to the proximal portion of the opening formed in the sidewall of the electrode.

8. The treatment tool according to claim 2, wherein, in the second position, the first end of the elastic member is located at an inner circumferential surface of the flow channel.

9. The treatment tool according to claim 2, wherein, in the electrode first position, the first end of the elastic member is deformed by application of an external force.

10. The treatment tool according to claim 9, wherein, in the electrode second position, the first end of the elastic member is not deformed.

11. The treatment tool according to claim 2, wherein, in the electrode first position, a tip of the first end of the elastic member is located in the flow channel, and
- wherein, in the electrode second position, the tip of the first end abuts an inner circumferential surface of the electrode or is located between an inner circumferential surface of the electrode and an outer circumferential surface of the electrode.

12. The treatment tool according to claim 2, wherein the through hole of the holder has an inclined surface that, in a direction from a proximal end of the holder toward a distal end of the holder, is inclined toward the electrode.

13. The treatment tool according to claim 12, wherein, in the electrode first position, the elastic member contacts the inclined surface, and
- wherein, in an electrode second position, the elastic member is spaced apart from the inclined surface.

14. The treatment tool according to claim 2, wherein the holder has a recess recessed from the through hole toward an outer circumference of the holder, and
- wherein the elastic member is provided in the recess.

15. The treatment tool according to claim 2, wherein the electrode is displaceable relative to the sheath between the electrode first position and the electrode second position by rotation of the electrode relative to the sheath around the longitudinal axis.

16. The treatment tool according to claim 2, wherein the electrode is displaceable relative to the sheath between the electrode first position and an electrode second position by operation of the hollow operation wire.

17. The treatment tool according to claim 2, wherein, when the elastic member is located at an elastic member second position, the elastic member is spaced apart from the holder.

18. The treatment tool according to claim 2, wherein a distal end of the elastic member is in contact with the holder.

19. A treatment tool, comprising:

a sheath;

an electrode located in the sheath, the electrode includes a flow channel formed along a longitudinal axis of the electrode and extending between a distal end and a proximal end of the electrode;

a holder fixed to a distal end of the sheath and having a through hole in which the electrode is inserted; and an elastic member located on an outer surface of the electrode, wherein the through hole of the holder has an inclined surface that, in a direction from a proximal end of the holder toward a distal end of the holder, is inclined toward the electrode, wherein, in an electrode first position, the elastic member contacts the inclined surface, and wherein, in an electrode second position, the elastic member is spaced apart from the inclined surface.

* * * * *